(12) United States Patent
Tochigi et al.

(10) Patent No.: US 7,559,263 B2
(45) Date of Patent: Jul. 14, 2009

(54) PRESSURE RESISTANCE INSPECTING METHOD AND PRESSURE RESISTANCE INSPECTING APPARATUS FOR HEAT EXCHANGERS

(75) Inventors: Masaharu Tochigi, Oyama (JP); Takashi Shida, Oyama (JP); Keiji Fukaura, Oyama (JP); Takumi Akatsuka, Oyama (JP)

(73) Assignee: Showa Denko K.K., Tokyo (JP)

( * ) Notice: Subject to any disclaimer, the term of this patent is extended or adjusted under 35 U.S.C. 154(b) by 253 days.

(21) Appl. No.: 11/578,557

(22) PCT Filed: Apr. 21, 2005

(86) PCT No.: PCT/JP2005/008109

§ 371 (c)(1),
(2), (4) Date: Oct. 16, 2006

(87) PCT Pub. No.: WO2005/103607

PCT Pub. Date: Nov. 3, 2005

(65) Prior Publication Data

US 2007/0234783 A1 Oct. 11, 2007

Related U.S. Application Data

(60) Provisional application No. 60/565,830, filed on Apr. 28, 2004, provisional application No. 60/628,545, filed on Nov. 18, 2004, provisional application No. 60/637,812, filed on Dec. 22, 2004, provisional application No. 60/641,743, filed on Jan. 7, 2005, provisional application No. 60/662,361, filed on Mar. 17, 2005.

(30) Foreign Application Priority Data

| Apr. 22, 2004 | (JP) | ............................. 2004-126661 |
| Nov. 12, 2004 | (JP) | ............................. 2004-328493 |
| Dec. 16, 2004 | (JP) | ............................. 2004-363861 |
| Dec. 28, 2004 | (JP) | ............................. 2004-379355 |
| Mar. 11, 2005 | (JP) | ............................. 2005-068563 |

(51) Int. Cl.
*G01M 19/00* (2006.01)

(52) U.S. Cl. .................. 73/865.8; 73/114.68

(58) Field of Classification Search ............. 73/114.68, 73/865.8
See application file for complete search history.

(56) References Cited

U.S. PATENT DOCUMENTS

| 3,630,596 | A | * | 12/1971 | Watkins ...................... 359/559 |
| 4,887,899 | A | * | 12/1989 | Hung ......................... 356/35.5 |
| 4,913,547 | A | * | 4/1990 | Moran ........................ 356/489 |
| 5,011,280 | A | * | 4/1991 | Hung ......................... 356/35.5 |

FOREIGN PATENT DOCUMENTS

JP        6-281373        10/1994

(Continued)

*Primary Examiner*—John Fitzgerald
(74) *Attorney, Agent, or Firm*—Oblon, Spivak, McClelland, Maier & Neustadt, P.C.

(57) ABSTRACT

A method of inspecting a heat exchanger for pressure resistance. The heat exchanger includes plural hollow refrigerant channel portions arranged in parallel and each having joints inside thereof, air passing clearances between respective adjacent pairs of refrigerant channel portions, and fins in the respective air passing clearances. The heat exchanger interior is pressurized, irradiated with light from one side, and a monochromatic image of the exchanger is captured by CCD cameras from the other side before and after the pressurization. Each image is divided into dots, luminance data of the dots of each image is converted into binary data items of white areas and black areas with reference to a threshold value, and the number of black areas is counted. The pressure resistance of the heat exchanger is judged based on an increase in the number of black areas after pressurization from the number of black areas before pressurization.

19 Claims, 25 Drawing Sheets

FOREIGN PATENT DOCUMENTS

| | | |
|---|---|---|
| JP | 2000-337821 | 12/2000 |
| JP | 2000 337821 | 12/2000 |
| JP | 2002 250611 | 9/2002 |
| JP | 2002-250611 | 9/2002 |

* cited by examiner

PRESSURE RESISTANCE INSPECTING METHOD AND PRESSURE RESISTANCE INSPECTING APPARATUS FOR HEAT EXCHANGERS

CROSS REFERENCE TO RELATED APPLICATIONS

This application is an application filed under 35 U.S.C. §111(a) claiming the benefit pursuant to 35 U.S.C. §119 (e) (1) of the filing dates of Provisional Applications No. 60/565, 830, No. 60/628,545. No. 60/637,812, No. 60/641,743 and No. 60/662,361 filed Apr. 28, 2004, Nov. 18, 2004, Dec. 22, 2004, Jan. 7, 2005, and Mar. 17, 2005, respectively, pursuant to 35 U.S.C. §111(b).

TECHNICAL FIELD

The present invention relates to pressure resistance inspecting methods and pressure resistance inspecting apparatus for heat exchangers having a plurality of hollow refrigerant channel portions arranged in parallel and each having joints inside thereof, air passing clearances between respective adjacent pairs of refrigerant channel portions, and fins arranged in the respective air passing clearances.

The term "aluminum" as used herein includes aluminum alloys in addition to pure aluminum.

BACKGROUND ART

Heat exchangers are in wide use which comprise a pair of aluminum headers arranged in parallel as spaced apart from each other, a plurality of flat heat exchange tubes of aluminum serving as hollow refrigerant channel portions, arranged in parallel between the pair of headers and having opposite ends jointed to the respective headers, and corrugated aluminum fins arranged in respective air passing clearances between respective adjacent pairs of heat exchange tubes and each joined to the pair of heat exchange tubes adjacent thereof.

The flat heat exchange tube comprises, for example, two flat walls positioned in parallel to each other, opposite side walls interconnecting the two flat walls respectively at opposite side edges thereof, and a plurality of reinforcing walls interconnecting the two flat walls, extending longitudinally thereof and arranged at a predetermined spacing between the opposite side walls, the heat exchange tube having parallel fluid passageways in the interior thereof, each of the reinforcing walls comprising a reinforcing wall ridge projecting inward from one of the flat walls and formed integrally therewith and a reinforcing wall ridge projecting inward from the other flat wall and formed integrally therewith, the reinforcing wall ridges being butted against and brazed to each other, the portions of the wall ridges brazed to each other providing an inside joint. (see the publication of JP-A No. 6-281373).

For the heat exchanger described above and comprising the flat heat exchange tube to have the required heat resistance, the reinforcing wall ridges need to be brazed to each other with a sufficient strength and free from brazing faults.

However, it is not easy to detect faults in the portions of the reinforcing wall ridges brazed to each other, i.e., in the inside joint, and the strength of the brazing joint between the wall ridges, and consequently it is presently impossible to inspect the heat exchanger for pressure resistance easily.

An object of the present invention, which has been accomplished in view of the above situation, is to provide a method of and an apparatus for inspecting heat exchangers for pressure resistance relatively easily and accurately.

DISCLOSURE OF THE INVENTION

To fulfill the above object, the present invention comprises the following modes.

1) A method of inspecting a heat exchanger for pressure resistance, the heat exchanger having a plurality of hollow refrigerant channel portions arranged in parallel and each having joints inside thereof, air passing clearances between respective adjacent pairs of refrigerant channel portions, and fins arranged in the respective air passing clearances, the method of inspecting a heat exchanger for pressure resistance being characterize by pressurizing interior of the heat exchanger, thereafter irradiating the heat exchanger with light from one side thereof with respect to the direction of passage of air therethrough and visually inspecting the heat exchanger from the other side thereof.

2) A method of inspecting a heat exchanger for pressure resistance according to par. 1) wherein the fins of the heat exchanger are visually inspected for deformation.

3) A method of inspecting a heat exchanger for pressure resistance according to par. 1) wherein the refrigerant channel portions are visually inspected for deformation.

4) A method of inspecting a heat exchanger for pressure resistance, the heat exchanger having a plurality of hollow refrigerant channel portions arranged in parallel and each having joints inside thereof, air passing clearances between respective adjacent pairs of refrigerant channel portions, and fins arranged in the respective air passing clearances, the method of inspecting a heat exchanger fop pressure resistance being characterize by pressurizing interior of the heat exchanger, irradiating the heat exchanger with light from one side thereof with respect to the direction of passage of air therethrough and capturing an image of the heat exchanger by image pickup means from the other side thereof before and after the pressurization, dividing each of the images into a plurality of dots, and judging the pressure resistance of the heat exchanger based on luminance data as to the dots of the images obtained before and after the pressurization.

5) A method of inspecting a heat exchanger for pressure resistance, the heat exchanger having a plurality of hollow refrigerant channel portions arranged in parallel and each having joints inside thereof, air passing clearances between respective adjacent pairs of refrigerant channel portions, and fins arranged in the respective air passing clearances, the method of inspecting a heat exchanger for pressure resistance being characterize by irradiating the heat exchanger with light from one side thereof with respect to the direction of passage of air therethrough, capturing an image of the heat exchanger by image pickup means from the other side thereof, dividing the image into a plurality of dots, thereafter pressurizing interior of the heat exchanger, capturing an image of the heat exchanger by image pickup means from the other side thereof continuously or intermittently after the start of the pressurization, dividing the image into a plurality of dots, and judging the pressure resistance of the heat exchanger based on luminance data as to the dots of the image obtained before the pressurization and on continuous variations or intermittent variations in luminance data as to the dots of the image obtained after the pressurization.

6) A method of inspecting a heat exchanger for pressure resistance according to par. 4) or 5) which includes capturing a plurality of images of a portion of the heat exchanger by the image pickup means from a plurality of directions, dividing each of the images into dots, and using luminance data as to the dots of the plurality of images of the same portion as a reference for judgment.

7) A method of inspecting a heat exchanger for pressure resistance according to par. 4) or 5) which includes capturing a monochromatic image of the heat exchanger by the image pickup means before and after the pressurization, dividing each of the monochromatic images into a plurality of dots, converting luminance data as to the dots of each of the images obtained before and after the pressurization into binary data items of white areas and black areas with reference to a predetermined reference value, counting the number of black areas of each monochromatic image, and using an increase in the number of black areas after the pressurization from the number of black areas before the pressurization as a reference for judgment.

8) A method of inspecting a heat exchanger for pressure resistance according to par. 4) or 5) which includes capturing a plurality of monochromatic images of a portion of the heat exchanger by the image pickup means from a plurality of directions, dividing each of the images into dots, converting luminance data as to the dots of each of the images obtained before and after the pressurization into binary data items of white areas and black areas with reference to a predetermined reference value, counting the number of black areas of each monochromatic image, and using an increase in the total number of black areas of all monochromatic images after the pressurization from the total number of black areas of all monochromatic images before the pressurization as a reference for judgment.

9) A method of inspecting a heat exchanger for pressure resistance according to par. 4) or 5) which includes capturing a monochromatic image of the heat exchanger by the image pickup means before and after the pressurization, dividing each the monochromatic images into a plurality of dots, converting luminance data as to the dots of each of the images obtained before and after the pressurization into binary data items of white areas and black areas with reference to a predetermined reference value to extract a pattern of white areas and black areas in each monochromatic image, and using the patterns obtained before and after the pressurization as a reference for judgment.

10) A method of inspecting a heat exchanger for pressure resistance according to par. 5) wherein the pressure to be applied to the interior of the heat exchanger is controlled based on continuous variations or intermittent variations in the luminance data as to the dots of the image obtained after the pressurization.

11) A method of inspecting a corrugated fin having crest portions, furrow portions and connecting portions each interconnecting the crest portion and the furrow portion, the method of inspecting a corrugated fin characterized by irradiating the corrugated fin with light from one side thereof with respect to the widthwise direction thereof, capturing a plurality of images of a portion of the corrugated fin from a plurality of directions on the other side thereof by the image pickup means, dividing each of the images into dots, and judging the state of the corrugated fin based on luminance data as to the dots of the plurality of images of the same portion.

12) A method of inspecting a corrugated fin according to par. 11) including capturing a plurality of monochromatic images of a portion of the corrugated fin from a plurality of directions by the image pickup means, dividing each of the monochromatic images into dots, converting luminance data as to the dots of each image into binary data items of white areas and black areas with reference to a predetermined threshold value, counting the number of black areas, and using the total number of black areas of all monochromatic images of the same portion as a reference for judgment.

13) A method of inspecting a corrugated fin according to par. 11) or 12) for use in a heat exchanger having a plurality of hollow refrigerant channel portions arranged in parallel and each having joints inside thereof, and air passing clearances between respective adjacent pairs of refrigerant channel portions, to inspect corrugated fins arranged in the respective air passing clearances.

14) An apparatus for inspecting a heat exchanger for pressure resistance, the heat exchanger having a plurality of hollow refrigerant channel portions arranged in parallel and each having joints inside thereof, air passing clearances between respective adjacent pairs of refrigerant channel portions, and fins arranged in the respective air passing clearances, the inspecting apparatus comprising pressurizing means for pressurizing interior of the heat exchanger, irradiating means disposed on one side of the heat exchanger with respect to the direction of passage of air therethrough for irradiating the heat exchanger with light, image pickup means for capturing an image of the heat exchanger from the other side of the heat exchanger opposite to the irradiating means with respect to the direction of passage of air, and processing means for dividing the images obtained by the image pickup means into a plurality of dots before and after the pressurization by the pressurizing means and judging the pressure resistance of the heat exchanger based on luminance data as to the dots of each of the images.

15) An apparatus for inspecting a heat exchanger for pressure resistance according to par. 14) wherein the image pickup means captures a plurality of images of a portion of the heat exchanger from a plurality of directions, and the processing means divides each of the images of the same portion into a plurality of dots and judges the pressure resistance of the heat exchanger based on luminance data as to the dots of each image.

16) An apparatus for inspecting a heat exchanger for pressure resistance according to par. 14) wherein the processing means divides a monochromatic image of the heat exchanger captured by the image pickup means before and after the pressurization into plurality of dots, converting luminance data as to the dots of each of the monochromatic images obtained before and after the pressurization into binary data items of white areas and black areas with reference to a predetermined reference value, counting the number of black areas of each monochromatic image, and judging the pressure resistance of the heat exchanger based on an increase in the number of black areas after the pressurization from the number of black areas before the pressurization.

17) An apparatus for inspecting a heat exchanger for pressure resistance according to par. 14) wherein the image pickup means captures a plurality of monochromatic images of a portion of the heat exchanger from a plurality of directions, and the processing means divides each of the monochromatic images of the same portion into dots, converts luminance data as to the dots of each image into binary data items of white areas and black areas with reference to a predetermined reference value, counts the number of black areas of each monochromatic image, and judges the pressure resistance of the heat exchanger based on an increase in the total number of black areas of all monochromatic images after the pressurization from the total number of black areas of all monochromatic images before the pressurization.

18) An apparatus for inspecting a heat exchanger for pressure resistance according to par. 14) wherein the processing means divides each of the monochromatic images of the heat exchanger captured by the image pickup means before and after the pressurization into dots, converts luminance data as to the dots of each of the images into binary data items of white areas and black areas with reference to a predetermined reference value to extract a pattern of white areas and black areas in each monochromatic image, and judges the pressure resistance of the heat exchanger based on the patterns obtained before and after the pressurization.

19) An apparatus for inspecting a heat exchanger for pressure resistance according to par. 14) wherein reflecting means is disposed on the other side of the heat exchanger opposite to the irradiating means with respect to the direction of passage of air for reflecting the light from the irradiating means at least once, and the image pickup means captures images reflected at the reflecting means.

20) An apparatus for inspecting a heat exchanger for pressure resistance according to par. 14) wherein the processing means judges the pressure resistance of the heat exchanger based on the luminance data as to the dots of the image before the pressurization and on continuous variations or intermittent variations in the luminance data as to the dots of the image after the pressurization.

21) An apparatus for inspecting a heat exchanger for pressure resistance according to par. 20) wherein the processing means divides each of monochromatic images of the heat exchanger captured by the image pickup means before and after the pressurization into a plurality of dots, converts luminance data as to the dots of each of the images into binary data items of white areas and black areas with reference to a predetermined reference value, counts the number of black areas in each monochromatic image and judges the pressure resistance of the heat exchanger based on the number of black areas before the pressurization and on continuous variations or intermittent variations in the number of black areas after the pressurization.

22) An apparatus for inspecting a heat exchanger for pressure resistance according to par. 20) wherein the image pickup means captures a plurality of monochromatic images of a portion of the heat exchanger from a plurality of directions, and the processing means divides each of the images of the same portion into a plurality of dots, converts luminance data as to the dots of each image into binary data items of white areas and black areas with reference to a predetermined reference value, counts the number of black areas in each monochromatic image and judges the pressure resistance of the heat exchanger based on the number of black areas before the pressurization and on continuous variations or intermittent variations in the number of black areas after the pressurization.

23) An apparatus for inspecting a heat exchanger for pressure resistance according to par. 20) wherein the processing means divides each of monochromatic images of the heat exchanger captured by the image pickup means before and after the pressurization into a plurality of dots, converts luminance data as to the dots of each of the images into binary data items of white areas and black areas with reference to a predetermined reference value to extract a pattern of white areas and black areas in each monochromatic image, and judges the pressure resistance of the heat exchanger based on the pattern before the pressurization and on continuous variations or intermittent variations in the pattern after the pressurization.

24) An apparatus for inspecting a heat exchanger for pressure resistance according to par. 20) wherein the processing means controls the pressure to be applied to the interior of the heat exchanger by the pressurizing means based on continuous variations or intermittent variations in the luminance data as to the dots of the image obtained after the pressurization.

25) An apparatus for inspecting a corrugated fin having crest portions, furrow portions and connecting portions each interconnecting the crest portion and the furrow portion, the apparatus comprising irradiating means disposed on one side of the corrugated fin with respect to the widthwise direction thereof for irradiating the corrugated fin with light, image pickup means disposed on the other side of the corrugated fin opposite to the irradiating means for capturing images of a portion of the corrugated fin from a plurality of directions, and processing means for judging the state of the corrugated fin based on luminance data as to the dots of the images of the same portion of the corrugated fin.

26) An apparatus for inspecting a corrugated fin according to par. 25) wherein the image pickup means captures a plurality of monochromatic images of a portion of the corrugated fin from a plurality of directions, and the processing means divides each of the monochromatic images of the same portion into dots, converts luminance data as to the dots of each image into binary data items of white areas and black areas with reference to a predetermined threshold value, counts the number of black areas of each monochromatic image and judges the state of the corrugated fin based on the total number of black areas of all monochromatic images.

27) An apparatus for inspecting a corrugated fin according to par. 25) for use in a heat exchanger having a plurality of hollow refrigerant channel portions arranged in parallel and each having joints inside thereof, and air passing clearances between respective adjacent pairs of refrigerant channel portions, to inspect corrugated fins arranged in the respective air passing clearances.

28) An apparatus for inspecting a corrugated fin for according to par. 25) wherein reflecting means is disposed on the other side of the corrugated fin opposite to the irradiating means with respect to the direction of passage of air for reflecting the light from the irradiating means at least once, and the image pickup means captures images reflected at the reflecting means.

29) A heat exchanger fabrication line comprising an apparatus according to any one of pars. 14) to 28).

In the event of a fault occurring in inside joints of the hollow refrigerant channel portion, or in the case where some inside joints are insufficient in joint strength, the application of pressure to the interior of the heat exchanger by the method according to pars. 1) to 3) breaks the inside joints, inflates the refrigerant channel portion and deforms the fin positioned in the air passing clearance. Accordingly, at least one of the channel portion and the fin can be checked for deformation by irradiating the heat exchanger with light from one side thereof and visually inspecting the heat exchanger from the other side thereof after the pressurization of the interior of the exchanger, whereby the pressure resistance of the heat exchanger can be judged. Thus, the heat exchanger can be inspected for pressure resistance easily. Moreover it is possible to reliably recognize the deformation of important portions, such as the refrigerant channel portion, portions of the headers close to the fins, and portions tacked by welding before joining by brazing.

In the event of a fault occurring in inside joints of the hollow refrigerant channel portion, or in the event of some inside joints failing to have a sufficient joint strength, the application of pressure to the interior of the heat exchanger by the method according to par. 4) breaks the inside joints, inflates the refrigerant channel portion and deforms the fin positioned in the air passing clearance. Accordingly when the method is practiced by irradiating the heat exchanger with light from one side thereof with respect to the direction of passage of air therethrough and capturing an image of the heat exchanger by image pickup means from the other side thereof before and after the pressurization and dividing each of the images into a plurality of dots, the images obtained before and after the pressurization are found different in the luminance data as to the dots. On the other hand, if the inside joints of the hollow refrigerant channel portion are free from faults and have a sufficiently great strength, the application of pressure to the interior of the heat exchanger causes no inflation of the channel portion and no deformation of the fin, with the result that the luminance data as to the dots of the image before the pressurization remains almost unaltered despite the pressurization. Thus, the heat exchanger can be inspected for pressure resistance with reference to such luminance data. Consequently, the heat exchanger can be inspected for pressure resistance easily and accurately. The method ensures inspection with good stability free from human errors or inadvertent errors to be involved in visual inspection, and free from the influence of ability of the inspector.

In the event of a fault occurring in inside joints of the hollow refrigerant channel portion, or in the event of some inside joints failing to have a sufficient joint strength, the application of pressure to the interior of the heat exchanger by the method according to par. 5) breaks the inside joints, greatly inflates the refrigerant channel portion and markedly deforms the fin positioned in the air passing clearance. In this case, the luminance data as to the dots of the image obtained after the pressurization continuously or intermittently varies greatly unlike the corresponding data before the pressurization. On the other hand, if the inside joints of the hollow refrigerant channel portion are free from faults and have a sufficiently great strength, the channel portion and the fin fail to deform greatly even if the heat exchanger is internally pressurized, and the luminance data as to the dots of the image before the pressurization remains almost unaltered despite the pressurization. Thus, the heat exchanger can be inspected for pressure resistance with reference to such luminance data as to the dots of images. Consequently, the heat exchanger can be inspected for pressure resistance easily and accurately. The method ensures inspection with good stability free from human errors or inadvertent errors to be involved in visual inspection, and free from the influence of ability of the inspector. Even when the inside joints are free from any break, the pressurization of the interior of the heat exchanger slightly deforms the refrigerant channel portion and the fin, but continuous variations or intermittent variations in the luminance data as to the dots of the image after the pressurization indicate to the inspector the deformation starting pressure and the deformation cessation pressure of the refrigerant channel portion and the fin. The heat exchanger can therefore be inspected for pressure resistance in greater detail. Furthermore, the kind of a particular joint fault in the inside joint can be identified with reference to the relationship between the applied pressure and the continuous or intermittent variations in the luminance data as to the dots. This makes it possible to work out a countermeasure for eliminating the joint fault. In the case where the inside joint of the refrigerant channel portion is extremely low in joint strength, the channel portion is likely to break abruptly before the internal pressure reaches a set value, whereas breaking pressure can be estimated from the correlation between the applied internal pressure and the continuous variations or intermittent variations in the luminance data as to the dots of the image after the pressurization. Moreover, the interior pressurization can be interrupted upon the variation in the luminance data in the image capturing range reaching a specified limit, whereby the inspecting apparatus can be prevented from becoming damaged or broken due to the breakdown of the entire heat exchanger Even if the fin provided in the air passing clearance is deformed to such an extent as not to affect the air passing performance, the heat exchanger can be inspected by the method described in par. 6) for pressure resistance easily and accurately. For example, if the fin is partly so inclined as not to influence the air passing performance, it is likely that the quantity of light passing through the air passing clearance will be insufficient, giving the dots of the resulting image inaccurate luminance data and leading to the judgment of unacceptability. On the other hand, in the case where a plurality of images of the inclined portion are captures by the image pickup means from a plurality of directions, it is likely that the luminance data as to the dots of the image obtained from one direction will be inaccurate, whereas the luminance data as to the dots of the image captured from another direction is accurate. Accordingly, when the pressure resistance of such a heat exchanger is judged based on these items of luminance data, there is no likelihood that the exchanger will be judged before or after the pressurization as being an unacceptable product of insufficient air passing performance.

The heat exchanger can be inspected for pressure resistance more accurately and easily by the method according to pars. 7) to 9). Especially, the method described in par. 8) has the following advantage. For example, even if the fin is deformed to an extent not to exert influence on the air passing performance, the heat exchanger can be inspected for pressure resistance accurately and easily. If the fin in a portion of the heat exchanger is so inclined as not to affect the air passing performance and when an image of the inclined portion is captured by the image pickup means from one direction, the quantity of light passing through the air passing clearance will be insufficient to result in an excessive number of black areas, leading to the judgment of unacceptable product. In the case where a plurality of images of the inclined portion are captured by the image pickup means from a plurality of directions, the monochromatic image obtained from one direction will be excessive in the number of binary data items of black areas in the image, whereas the monochromatic images captured from other directions will be smaller in the number of binary data items, i.e., of black areas. When the pressure resistance of the heat exchanger is judged based on the sum of these numbers of black areas, it is unlikely that the heat exchanger will be judged before the pressurization as being an unacceptable product of low air passing performance.

The method according to par. 9) further has the following advantage. The application of pressure to the interior of the heat exchanger causes a break in inside joints of the hollow refrigerant channel portion, markedly deforming the channel portion and the fin and altering the pattern of white areas and black areas in the image. Additionally, the deformation of the heat exchanger in its entirety and distortion thereof or a flicker will alter the pattern of white areas and black areas in the image. However, the pattern of white areas and black areas resulting from a break in inside joints of the channel portion and the consequent deformation of the channel portion and the fin differs from the pattern of white areas and black areas which is attributable to the deformation and distortion of the entire heat exchanger and a flicker. Accordingly when the pattern before the pressurization and the pattern after the pressurization are used as a reference for judgment, it is possible to discriminate between the deformation of the channel portion and the fin, and the deformation and distortion of the entire exchanger or a flicker. This ensures the inspection of pressure resistance with improved accuracy.

The heat exchanger can be inspected for pressure resistance by the method according to par. 10) without breaking the exchanger.

The method described in par. 11) comprises capturing a plurality of images of the same portion of the corrugated fin by the image pick means from a plurality of directions, dividing each of the images into dots, and judging the state of the corrugated fin based on luminance data as to the dots of the plurality of images of the same portion. Even if the corrugated fin is so deformed as not to exert influence on the air passing performance, the state of the fin can therefore be judged easily and accurately.

For example, even if the corrugated fin is deformed to an extent not to influence the air passing performance, the state of the fin can be inspected accurately and easily by the method according to par. 12). If some connecting portions of the corrugated fin are so inclined as not to affect the air passing performance and when an image of the inclined portions is captured by the image pickup means from one direction, the quantity of light passing through the clearances between respective adjacent pairs of connecting portions will be insufficient to result in an excessive number of black areas, leading to the judgment of unacceptable product. In the case where a plurality of images of the inclined portions are captured by the image pickup means from a plurality of directions, the monochromatic image obtained from one direction will be excessive in the number of binary data items of black areas in the image, whereas the monochromatic images captured from other directions will be smaller in the number of binary data items, i.e., of black areas. When the state of the corrugated fin is judged based on the sum of these numbers of black areas, it is unlikely that the fin will be judged before the pressurization as being an unacceptable product.

When for example, the total number of black areas in all monochromatic images is greater than a threshold value in practicing the method described in par. 13), the corrugated fin can be judged as being unacceptable without pressure resistance inspection.

The apparatus described in par. 14) has the same advantages as the methods described in pars. 4) and 5).

The apparatus described in par. 15) has the same advantage as the method described in pars. 6).

The apparatus described in pars. 16) to 18) has the same advantages as the methods described in pars. 7) and 9).

With the apparatus described in par. 19), the reflecting means reflects the light from the irradiating means at least once. This makes it possible to position the image pickup means at a greater distance from the heat exchanger. If the image pickup means has an angle of view, one pickup means can therefore be given a wider image pickup range. Accordingly, the image pickup means can be reduced in number to render the apparatus less costly. Further since the light emitted by the irradiating means is reflected by the reflecting means at least once, the space to be occupied by the entire apparatus can be relatively small even if the image pickup means is at a greater distance from the heat exchanger. Additionally, the heat exchanger, irradiating means and reflecting means can be arranged in conformity with the location where the apparatus is to be installed.

The apparatus according to par. 20) has the same advantage as the method of par. 5).

The apparatus according to pars. 21) to 23) has the same advantages as the method of pars. 7) to 9).

The apparatus according to par. 24) has the same advantage as the method of par. 10).

The apparatus according to pars. 25) and 26) has the same advantages as the methods of pars. 11) and 12).

With the apparatus described in par. 27), the reflecting means reflects the light from the irradiating means at least once. This makes it possible to position the image pickup means at a greater distance from the corrugated fin. If the image pickup means has an angle of view, one pickup means can therefore be given a wider image pickup range. Accordingly, the image pickup means can be reduced in number to render the apparatus less costly. Further since the light emitted by the irradiating means is reflected by the reflecting means at least once, the space to be occupied by the entire apparatus can be relatively small even if the image pickup means is at a greater distance from the corrugated fin. Additionally, the corrugated fin, irradiating means and reflecting means can be arranged in conformity with the location where the apparatus is to be installed.

BEST MODE OF CARRYING OUT THE INVENTION

Figure 1:
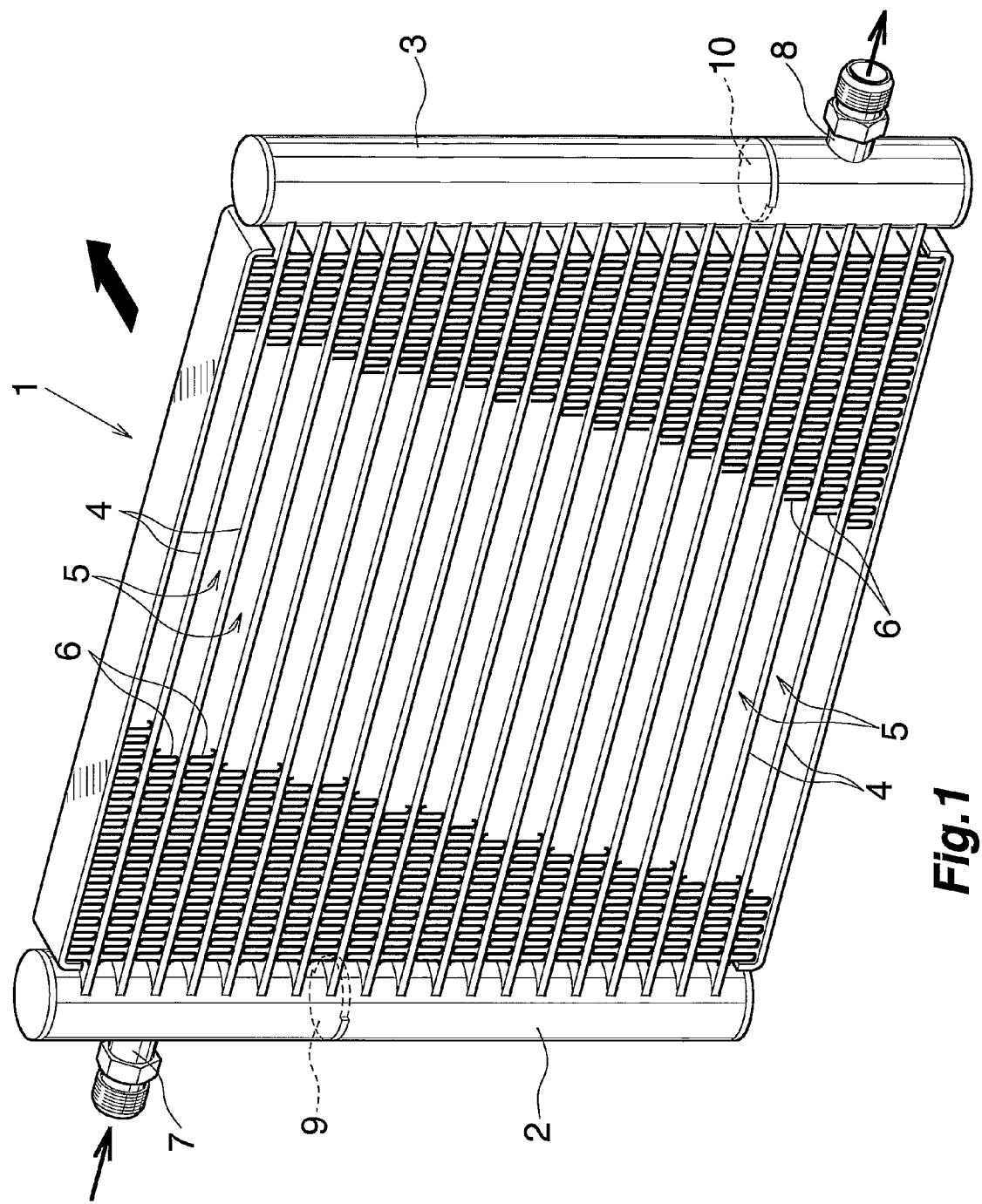
FIG. 1 is a perspective view showing an example of heat exchanger to be inspected for pressure resistance by a method and apparatus of the invention.

Embodiments of the invention will be described below with reference to the drawings. Throughout the drawings, like parts are designated by like reference numerals and will not be described repeatedly.

In the following description of refrigerant channel portions of the heat exchanger, the upper and lower sides, and left- and right-hand sides of FIGS. 2 and 3 will be referred to as "upper," "lower," "left" and "right," respectively.

Figure 2:
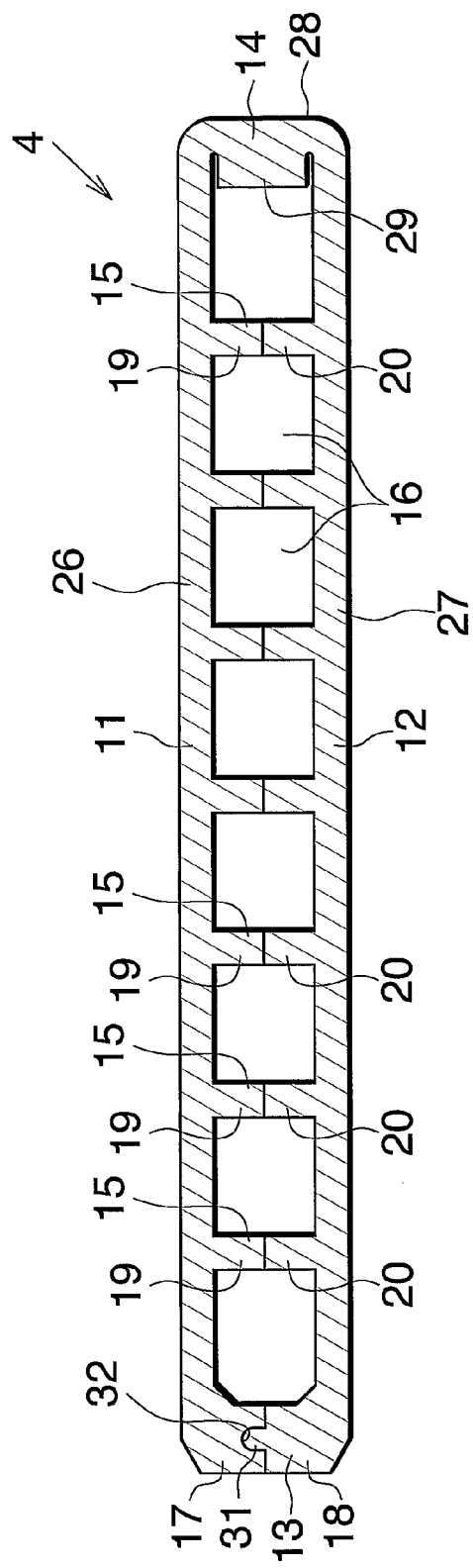
FIG. 2 is an enlarged cross sectional view showing a flat heat exchange tube of the heat exchanger of FIG. 1.
Figure 3:
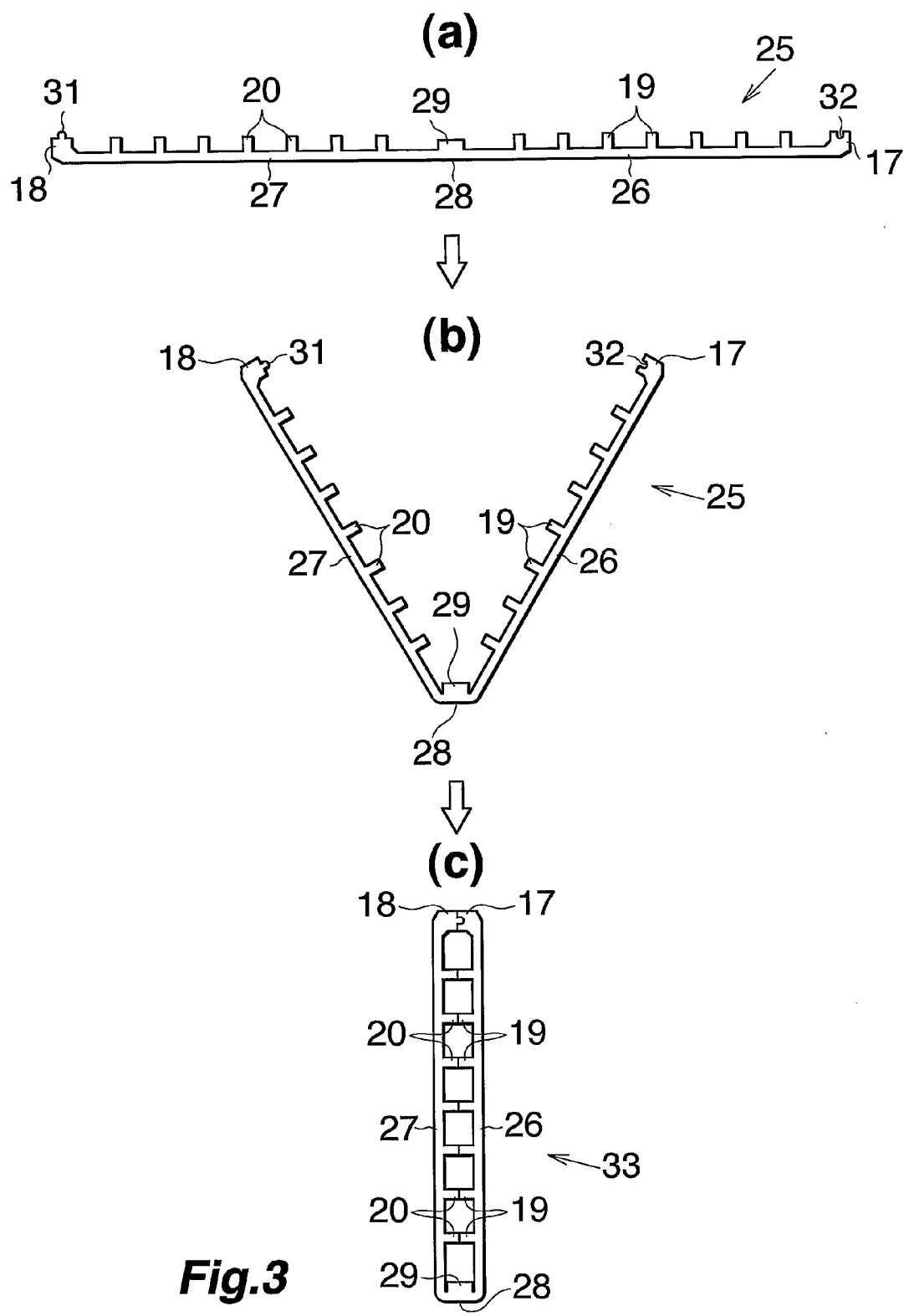
FIG. 3 is a diagram showing a process for fabricating the flat heat exchange tube of FIG. 2.

FIG. 1 shows an example of heat exchanger to be inspected for pressure resistance by a method of the invention, FIG. 2 shows an example of flat heat exchange tube serving as the refrigerant channel portion for use in the heat exchanger, and FIG. 3 shows a process for fabricating the flat heat exchange tube shown in FIG. 2.

The heat exchanger 1 shown in FIG. 1 is used as a condenser in motor vehicle air conditioners and comprises a pair of headers 2, 3 arranged in parallel as spaced apart from each other, a plurality of flat heat exchange tubes 4 (hollow refrigerant channel portions) of aluminum arranged in parallel between the two headers 2, 3 and having opposite ends joined to the respective headers 2, 3, corrugated aluminum fins 6 arranged in respective air passing clearances 5 between respective adjacent pairs of heat exchange tubes 4 and each brazed to the pair of heat exchanges tubes 4 adjacent thereto, an inlet pipe 7 connected to the upper end of peripheral wall of the first 2 of the headers, an outlet pipe 8 connected to the lower end of peripheral wall of the second 3 of the headers, a first partition 9 provided inside the first header 2 and positioned above the midportion thereof, and a second partition 10 provided inside the second header 3 and positioned below the midportion thereof. The number of refrigerant tubes 4 positioned above the first partition 9, the number of refrigerant tubes 4 between the first partition 9 and the second partition 10 and the number of refrigerant tubes 4 positioned below the second partition 10 decrease from above downward to provide groups of channels. A refrigerant flowing into the inlet pipe 7 in a vapor phase flows zigzag through the units of channel groups in the condenser before flowing out from the outlet pipe 8 in a liquid phase.

Along with a compressor and an evaporator, the heat exchanger 1, serving as a condenser, provides a refrigeration cycle wherein a chlorofluorocarbon refrigerant is used, and the refrigerant cycle is installed, for example, in a motor vehicle as a motor vehicle air conditioner.

For use in a refrigeration cycle which comprises a compressor, gas cooler, evaporator, pressure reducing device and an intermediate heat exchanger for subjecting the refrigerant flowing out from the gas cooler and the refrigerant flowing out of the evaporator to heat exchange and where $CO_2$ or like supercritical refrigerant is used, the heat exchanger 1 may be used as the gas cooler or evaporator. The refrigeration cycle is installed in vehicles, for example, in a motor vehicle to serve as a motor vehicle air conditioner.

With reference to FIG. 2, the heat exchange tube 4 comprises upper and lower flat walls 11, 12 (a pair of flat walls) opposed to each other, left and right opposite side walls 13, 14 interconnecting the upper and lower walls 11, 12 at their left and right side edges, and a plurality of reinforcing walls 15 interconnecting the upper and lower walls 11, 12, extending longitudinally of the tube and spaced from one another by a predetermined distance as positioned between the side walls 13, 14. The tube 4 has a plurality of parallel fluid passageways 16 in its interior. Although not shown, a plurality of communication holes are formed in each of all the reinforcing walls 15 so as to be positioned in a staggered arrangement when the tube is seen from above in its entirety for causing each adjacent pair of fluid passageways 16 to communicate with each other.

The left side wall 13 comprises a side wall ridge 17 projecting downward from the left side edge of the upper wall 11 and formed integrally therewith, and a side wall ridge 18 projecting upward from the left side edge of the lower wall 12 and formed integrally therewith. The side wall ridges 17, 18 are butted against and brazed to each other, whereby the left side wall 13 is formed. The right side wall 14 is integral with the upper and lower walls 11, 12.

Each reinforcing wall 15 comprises a reinforcing wall ridge 19 projecting downward from the upper wall 11 and integral therewith, and a reinforcing wall ridge 20 projecting upward from the lower wall 12 and integral therewith, and is formed by butting these ridges 19, 20 against each other and brazing the ridges 19, 20 to each other. The brazed portions of the ridges 19, 20 provides an inside joint.

The heat exchange tube 4 is fabricated from a tube making flat metal plate 25 as shown in FIG. 3(a). The metal plate 15 is made of an aluminum brazing sheet having a brazing material layer over opposite surfaces thereof, and comprises a flat upper wall forming portion 26 (flat wall forming portion), a flat lower wall forming portion 27 (flat wall forming portion), a connecting portion 28 interconnecting the upper and lower wall forming portions 26, 27 for making the right side wall 14, side wall ridges 17, 18 integrally projecting upward respectively from the upper wall forming portion 26 and the lower wall forming portion 27 each at a side edge thereof opposite to the connecting portion 28 for making the left side wall 13, and a plurality of reinforcing wall ridges 19, 20 projecting upward respectively from the upper wall forming portion 26 and the lower wall forming portion 27 integrally therewith and arranged at a predetermined spacing in the left-right direction. The reinforcing wall ridges 19 on the upper wall forming portion 26 and the reinforcing wall ridges 20 on the lower wall forming portion 27 are symmetrical about a widthwise center line of the plate 25. The side wall ridges 17, 18 and all reinforcing wall ridges 19, 20 are equal in height. The connecting portion 28 is integrally provided, over a major area thereof except the left and right opposite side edges thereof, with a positioning ridge 29 extending over the entire length thereof. A projection 31 is formed on the top end of the side wall ridge 18 on the lower wall forming portion 27 and extends longitudinally thereof over the entire length, and a groove 32 for the projection 31 to be forced in is formed in the top end of the side wall ridge 17 on the upper wall forming portion 26 and extends longitudinally thereof over the entire length.

Figure 13:
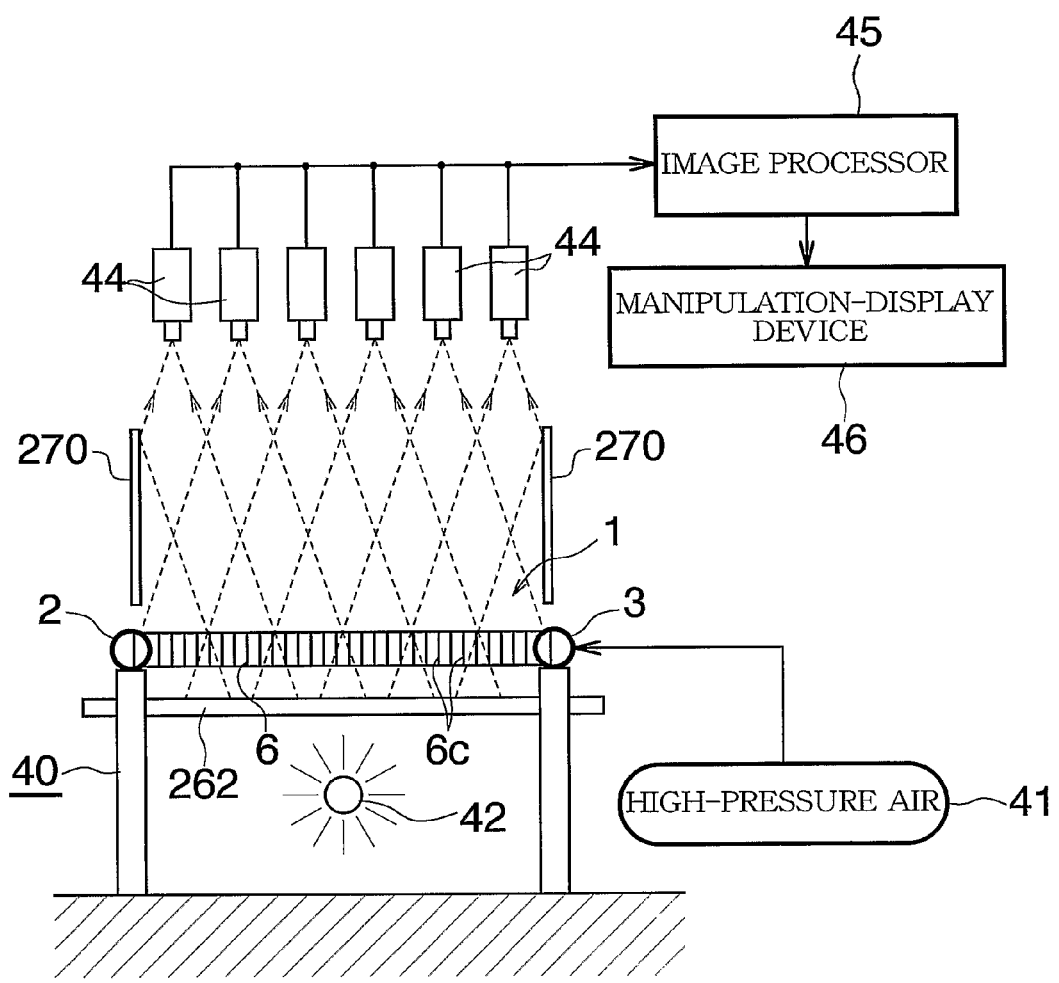
FIG. 13 is a diagram schematically showing the construction of a second embodiment of pressure resistance inspecting apparatus of the invention for heat exchangers.

The tube making metal plate 25 is progressively folded at the left and right opposite side edges of the connecting portion 28 by roll forming [see FIG. 13(*b*)], and is finally folded into a hairpin form to butt the inner side wall ridges 17, 18, as well as each corresponding pair of reinforcing wall ridges 19, 20, against each other and to force the projection 31 into the groove 32 by a press fit to obtain a folded body 33 [see FIG. 3(*c*)]. The side wall ridges 17, 18, as well as each corresponding pair of reinforcing wall ridges 19, 20, are brazed to each other at their top ends. Thus, the heat exchange tube 4 is fabricated. At this time, the left side wall 13 is provided by the side wall ridges 17, 18 brazed to each other, the right side wall 14 by the connecting portion 28, the upper wall 11 by the upper wall forming portion 26, the lower wall 12 by the lower wall forming portion 27, and each reinforcing wall 15 by the corresponding pair of ridges 19, 20 brazed to each other. The heat exchange tubes 4 are made simultaneously with the fabrication of the heat exchanger 1.

The corrugated fin 6 comprises crest portions 6*a*, furrow portions 6*b* and flat connecting portions 6*c* each interconnecting the crest portion 6*a* and the furrow portion 6*b*. The connecting portion 6*c* is provided with a plurality of louvers 6*d* arranged in parallel (see FIGS. 10 and 11).

Figure 4:
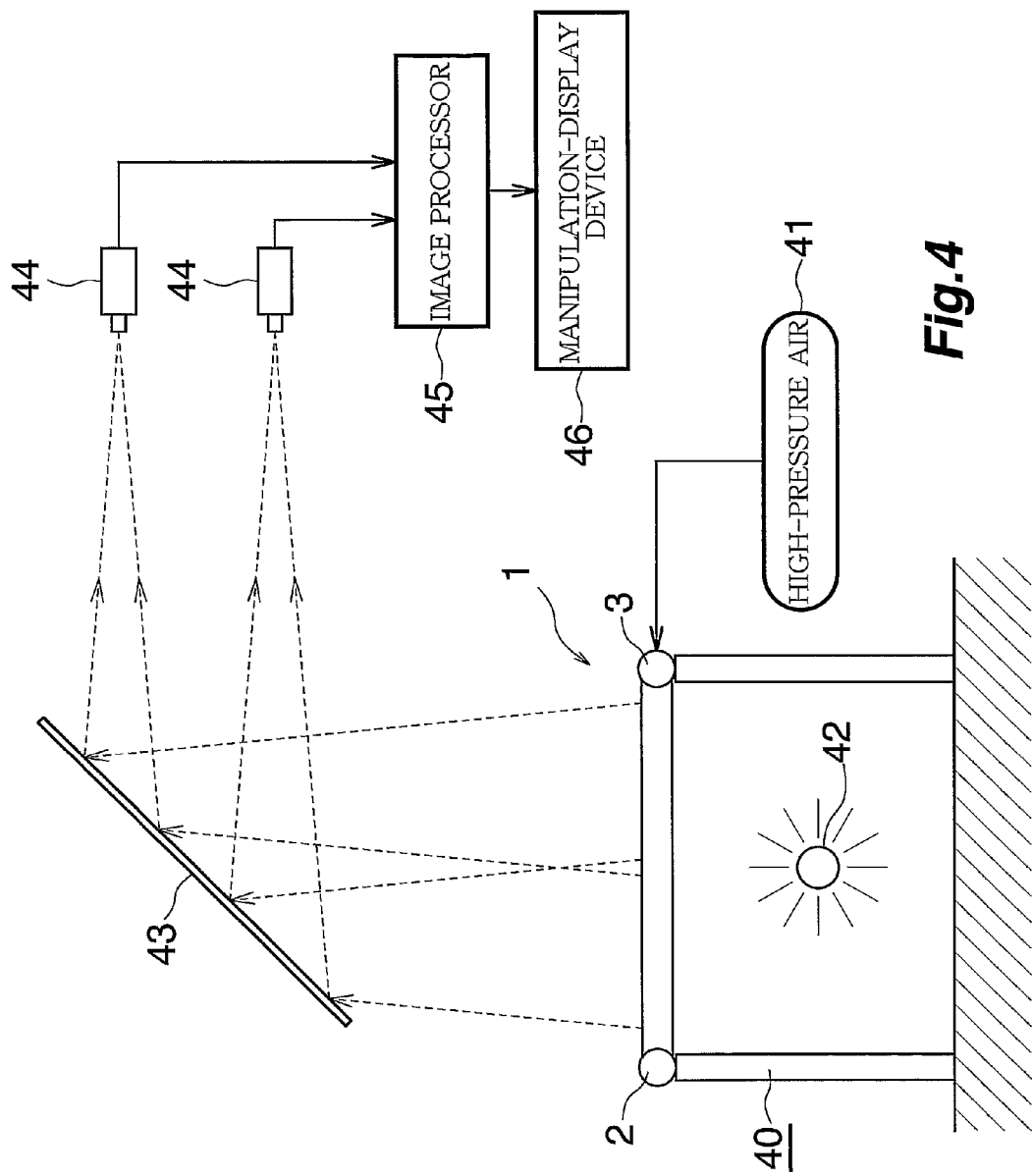
FIG. 4 is a diagram schematically showing the construction of a first embodiment of pressure resistance inspecting apparatus of the invention for heat exchangers.

FIG. 4 schematically shows the construction of a first embodiment of pressure resistance inspecting apparatus for heat exchangers.

With reference to FIG. 4, the pressure resistance inspecting apparatus comprises a holder 40 (holding means) for holding the heat exchanger 1 in a horizontal position, a high-pressure air supply device 41 (pressurizing means) for supplying high-pressure air to the interior of the heat exchanger 1 as sealed off and held by the holder 40 to pressurize the interior of the exchanger 1, an illuminator 42 (irradiating means) for irradiating the heat exchanger 1 held by the holder 40 with light from below, a reflector 43 (reflecting means) comprising, for example, a mirror disposed above the heat exchanger 1 held by the holder 40 for guiding the light from below sideways, i.e., rightward in the present embodiment, by reflecting the light once, CCD cameras 44 (image pickup means) for capturing a reflected image from the reflector 43, an image processor 45 (processing means), and a manipulation-display device 46 for the user to manipulate the apparatus therewith and displaying the result of pressure resistance inspection.

The holder 40 holds the two headers 2, 3 of the heat exchanger 1 so as not to close the air passing clearances 5.

An image of the heat exchanger 1 irradiated with light from below by the illuminator 42 is reflected from the reflector 43 and captured by each of the CCD cameras 44 as a monochromatic image, and the resulting image signal is fed from the cameras 44 to the image processor 45.

The image processor 4.5 divides the area of the monochromatic image captured by the CCD cameras 44 into dots (pixels), converts the luminance data as to the dots into binary data items, i.e., white areas and black areas, with reference to a predetermined threshold value, and counts up the number of black areas of the monochromatic image. While the interior of the heat exchanger 1 is pressurized with the high-pressure air supplied thereto by the air supply device 41, the image processor 45 compares the number of black areas representing the state of interior of the heat exchanger 1 before pressurization with the number of black areas resulting from the pressurization, judges the pressure resistance of the heat exchanger 1 based on the increase in the number of black areas due to the pressurization from the number of black areas before the application of pressure, and feeds the result of judgment to the manipulation-display device 46. The term "black areas" referred to indicates light blocking portions and means the portions where the headers 2, 3, heat exchange tubes 4 and corrugated fins 6 are present, and an increase in the number of black areas after the pressurization results from the deformation of the heat exchange tube 4 only, the corrugated fin 6 only, or deformation of both the heat exchange tube 4 and corrugated fin 6. The meaning of such black areas and the cause of the increase in the number of black areas after the pressurization are common herein and in the appended claims.

FIGS. 5 to 9 show the construction of the pressure resistance inspecting apparatus shown in FIG. 4 in detail. In the following description of the specific construction of the inspecting apparatus, the upper and lower sides of FIG. 5 will be referred to as "upper" and "lower," the left- and right-hand sides of FIG. 5 as "front" and "rear," and the left- and right-hand sides of FIG. 6 as "left" and "right."

Figure 5:
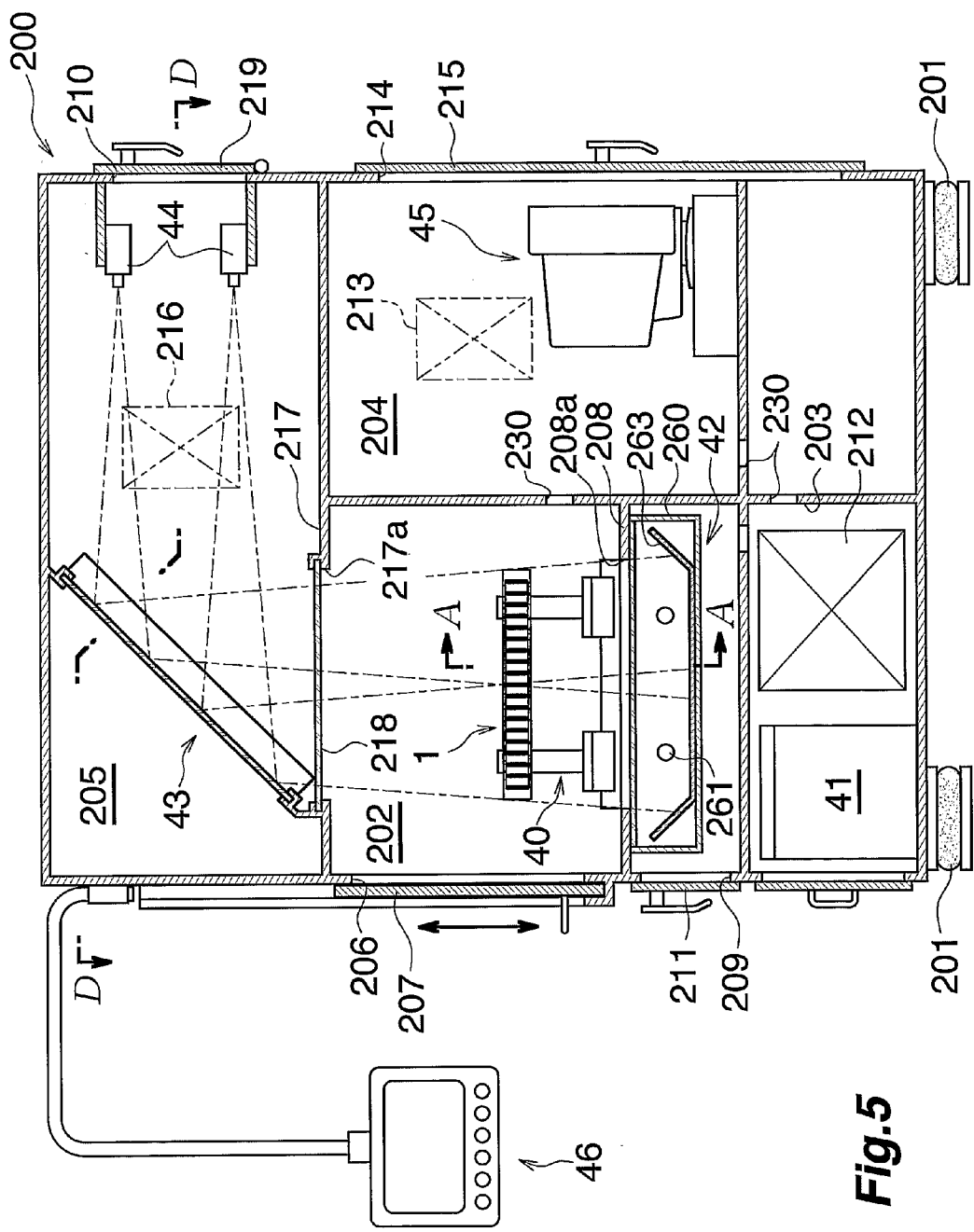
FIG. 5 is a view in vertical section showing in detail the construction of the pressure resistance inspecting apparatus of the invention for heat exchangers as it is seen from the right side thereof.

With reference to FIG. 5, one housing 200 has arranged therein the holder 40, high-pressure air supply device 41, illuminator 42, reflector 43, CCD cameras 44 and image processor 45 of the pressure resistance inspecting apparatus. The manipulation-display device 46 is disposed outside the housing 200. The inspecting apparatus is incorporated into a fabrication line for heat exchangers 1. The housing 200 is provided on the floor of a plant wherein the heat exchanger fabrication line is installed, with a seismic isolation device 201 interposed therebetween.

Provided inside the housing 200 are a first chamber 202 having the holder 40 and the illuminator 42 arranged therein, a second chamber 203 positioned under the first chamber 202 and having the high-pressure air supply device 41 disposed therein, a third chamber 204 positioned in the rear of the first chamber 202 and having the image processor 45 disposed therein, and a fourth chamber 205 disposed above both the first and third chambers 202, 204 and having arranged therein the reflector 43 and the CCD cameras 44. The housing 200 has a structure comprising planes, i.e., six metal plates providing the ceiling, floor and peripheral walls of the housing 200, for example, steel plates having a thickness of at least 10 mm, for supporting the load on the housing 200. The first to third chambers 202, 203, 204 are held in communication through air ports 230 formed in the partition walls.

The first chamber 202 has a front wall provided with an inlet-outlet opening 206 for the heat exchanger 1 to be inspected, and the opening 206 is closable with a vertically movable door 207. The interior of the first chamber 202 is divided into upper and lower two spaces by a partition plate 208 provided at a lower portion of inside of the chamber 202. The holder 40 is provided in the upper space, and the illuminator 42 in the lower space. The partition plate 208 has an opening 208*a* larger than the heat exchanger 1 to be inspected and permitting the light from the illuminator 42 to pass therethrough. The front wall of the first chamber 202 has an inspection opening 209 at a level corresponding to the lower space for inspecting the illuminator 42 therethrough. The opening 209 is closed with an openable door 211.

Attached to the left side wall of the second chamber 203 is a blower 212 (positive pressure holding means) for admitting outside air into the housing 200 to hold the inside of the first to third chambers 202, 203, 204 at a positive pressure. Although not shown, the blower 212 is provided with a filter for preventing ingress of dust into the housing 200.

The third chamber 204 has a right side wall provided with an air conditioner 213 for circulating air through the interior of the chamber 204 to maintain a constant temperature. The third chamber 204 has a rear wall provided with an inspection opening 214 for inspecting the image processor 45 therethrough and a door 215 for opening the opening 214.

The fourth chamber 205 is held closed independently of the other chambers 202 to 204. The fourth chamber 205 has a right side wall provided with an air conditioner 216 for maintaining the interior of the fourth chamber 205 at a constant temperature by circulating air therethrough. A partition wall 217 separating the fourth chamber 204 from the first and third chambers 202, 204 has an opening 217a in a front portion thereof, i.e., in a portion thereof corresponding to the first chamber 202. The opening 217a is hermetically closed with a light transmitting plate 218 made, for example, of glass. The opening 217a is so sized that an overall image of the heat exchanger 1 as held by the holder 40 can be reflected from the reflector 43 toward the CCD cameras 44. The rear wall of the fourth chamber 205 has an inspection opening 210 for inspecting the cameras 44 therethrough. The opening 210 is openable with a door 219.

Figure 6:
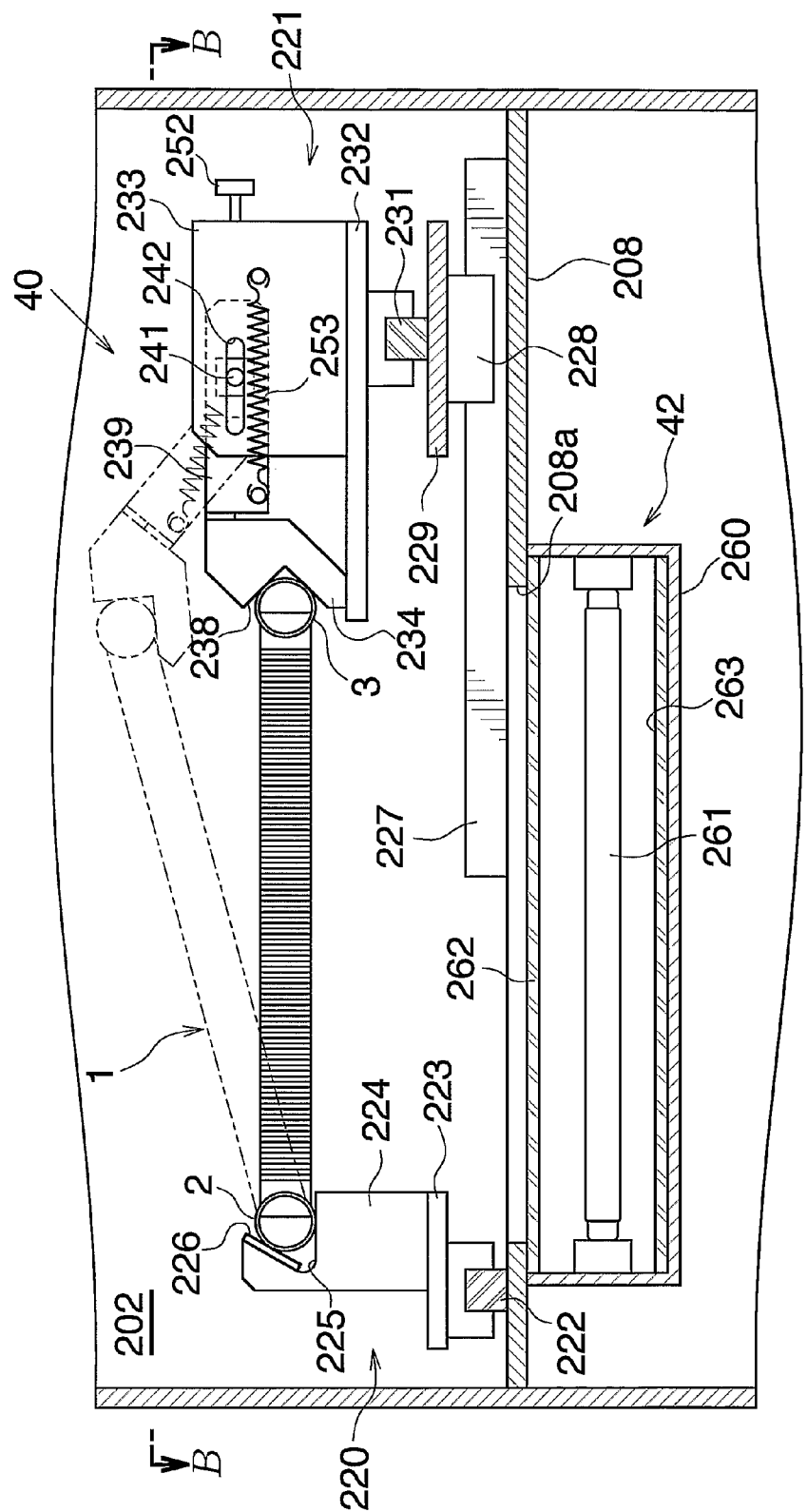
FIG. 6 is an enlarged view in section taken along the line A-A in FIG. 5.
Figure 7:
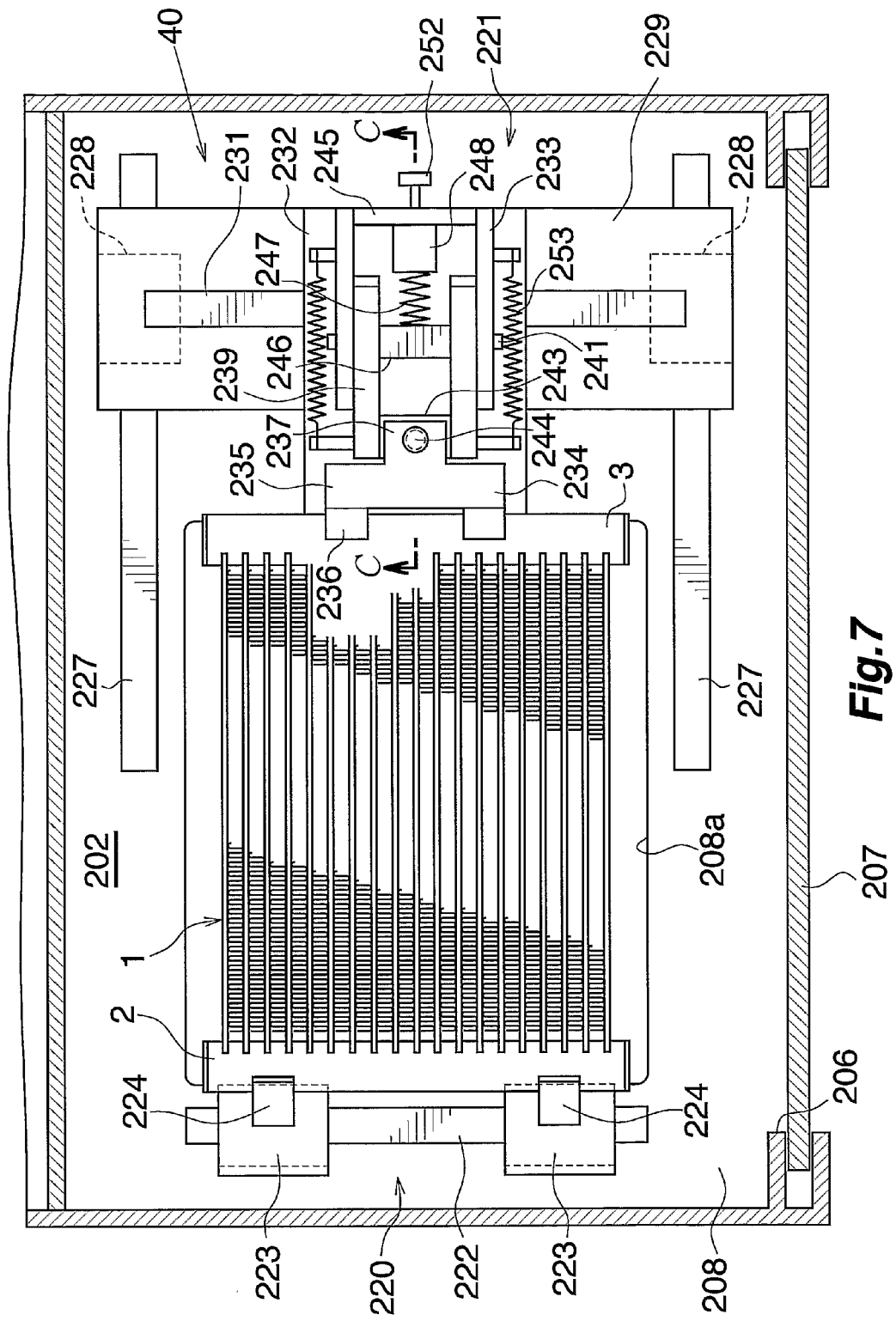
FIG. 7 is a view in section taken along the line B-B in FIG. 6.
Figure 8:
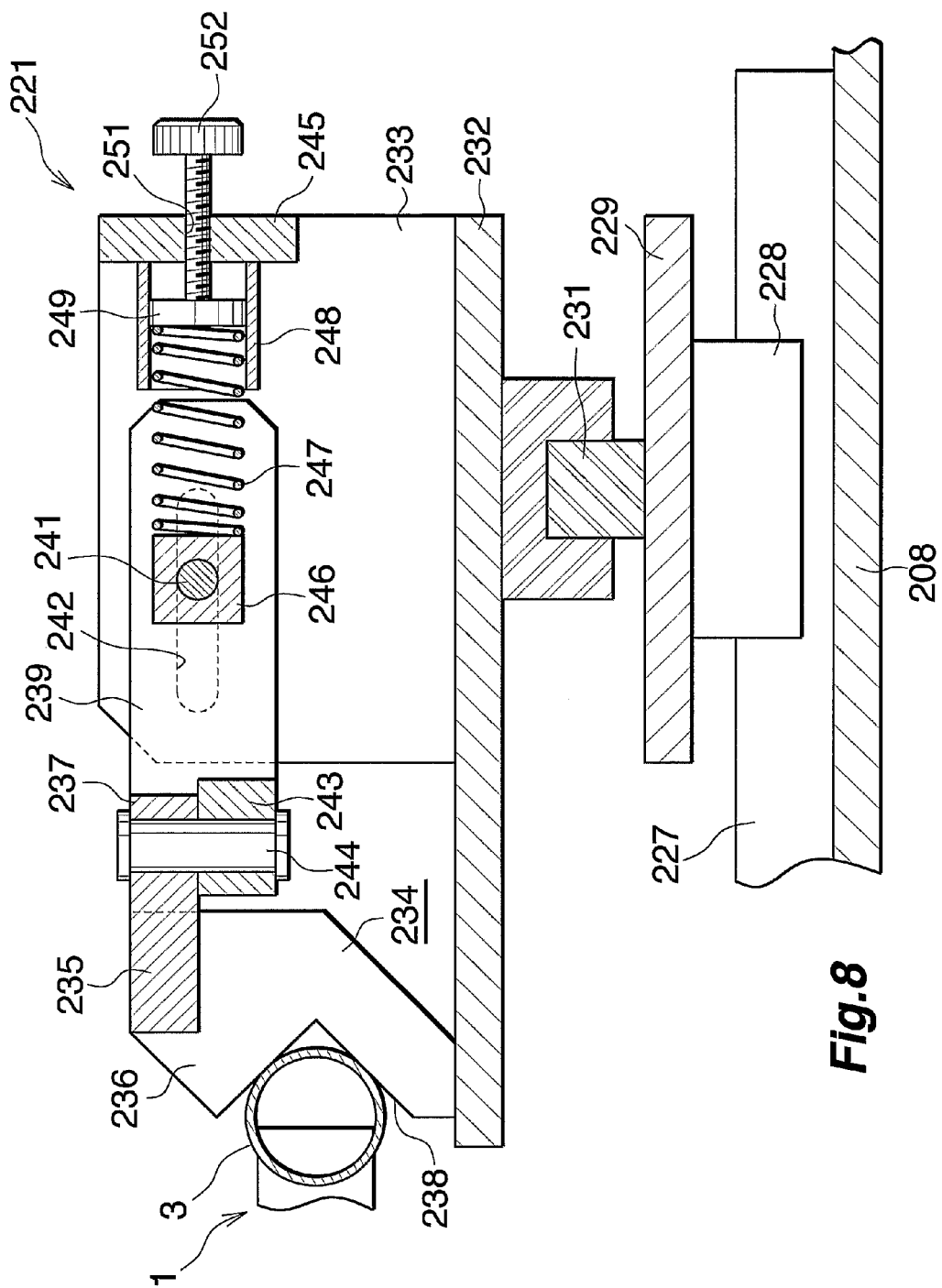
FIG. 8 is an enlarged view in section taken along the line C-C in FIG. 7.
Figure 9:
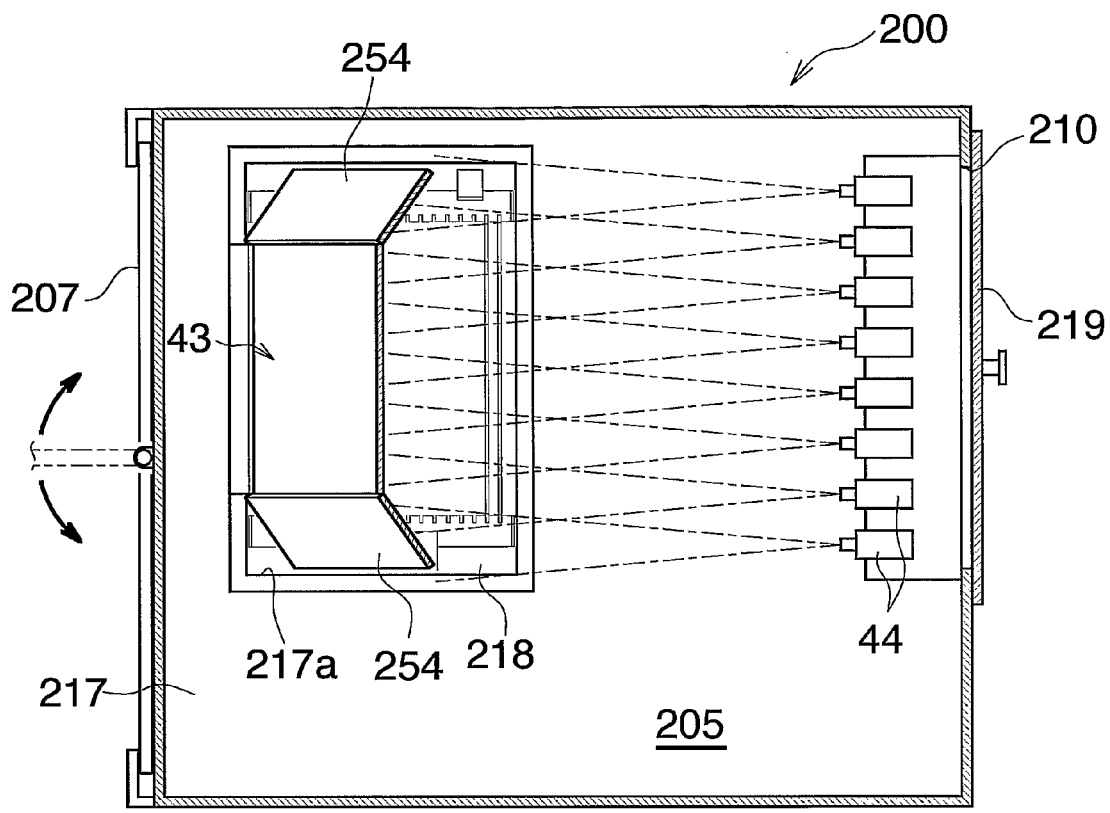
FIG. 9 is a view in section taken along the line D-D in FIG. 5.

With reference to FIGS. 6 to 8, the holder 40 comprises a first clamp device 220 mounted on the partition plate 208 for holding the header 2 of the heat exchanger 1 to be inspected, and a second clamp device 221 mounted on the partition plate 208 for holding the other header 3 of the exchanger 1 to be inspected.

The first clamp device 220 comprises a guide 222 fixedly mounted on a portion of the partition plate 208 on the left side of the opening 208a thereof and extending in the front-rear direction, front and rear two base plates 223 movable along the guide 222 and fixedly positionable on a desired portion of the guide 222, and a fixed clamp member 224 provided on each of the base plates 223 and projecting upward therefrom. The base plates 223 can be fixed each at a desired position on the guide 22, whereby the two fixed clamp members 224 are adjustable in position with respect to the front-rear direction in accordance with the length of the header 2 of the heat exchanger 1 to be inspected. Each clamp member 224 has a recessed portion 225 having an opening facing rightward for the header 2 to partly fit in. The upper inside part of the recessed portion 225 is provided with a slip preventing member 225 made, for example, of rubber.

The second clamp device 221 comprises a pair of guides 227 fixed respectively to the front and rear portions of the partition plate 208 on opposite sides of the opening 208a thereof and extending in the left-right direction, saddles 228 movable along the respective guides 227 and each fixedly positionable on a desired portion of the guide 227, a rail support plate 229 interconnecting and fixed to the front and rear saddles 228, a rail 231 mounted on the support plate 229 and extending in the front-rear direction, a base plate 232 mounted on the rail 231, for example, by an unillustrated straightly movable guide and free to move along the rail 231 in the front-rear direction, a pair of supports 233 upstanding from the base plate 232 and spaced apart in the front-rear direction, and a movable clamp member 234 mounted on the supports 233. The saddles 228 can be fixedly positioned each on a desired portion of the guide 227, so that the position of the movable clamp member 234 is adjustable in the left-right direction in accordance with the left-to-right size of the heat exchanger 1 to be inspected. The base plate 232 is movable along the rail 231, rendering the movable clamp member 234 free to move longitudinally of the header 3 of the heat exchanger 1.

The movable clamp member 234 comprises a base 235 elongated in the front-rear direction, and a pair of clamp portions 236 provided as spaced apart in the front-rear direction on the base 235. The base 235 has a bracket 237 projecting rightward from the lengthwise midportion thereof. Each of the clamp portions 236 has a recessed portion 238 having an opening facing leftward when holding the exchanger 1 for the other header 3 of the exchanger to fit in partly.

The movable clamp member 234 is attached to the supports 233 by a pair of front and rear arms 239. A rod 241 extending in the front-rear direction is fixedly inserted through the arms 239, and the portions of the rod 241 projecting outward in the front-rear direction beyond the arms 239 are rotatably and leftwardly or rightwardly movably fitted in slits 242 formed in the respective supports 233, elongated in the front-rear direction and positioned at the same level as the rod. A support plate 243 interconnects and is fixed to the left ends of the two arms 239. The bracket 237 of the movable clamp member 234 has a right end portion placed on the support plate 243 and attached thereto by a pin 244 extending upward or downward so as to be rotatable about the axis of the pin 244. The movable clamp member 234 is always biased leftward, i.e., toward the fixed clamp member 224 relative to the supports 233 by a compression coil spring 247 (biasing means) provided between a spring mount plate 245 and a spring retainer 246. The spring mount plate 245 is fixedly disposed between the right ends of the supports 233. The spring retainer 246 is rotatably fitted around the rod 241 and disposed between the two arms 239. The spring 247 has a left end bearing on the spring retainer 246. A hollow cylindrical spring holding member 248 is secured to the left side face of the spring mount plate 245. A spring retainer 249 is provided in the spring holding member 248 so as to be movable in the left-right direction. The spring 247 has a right end inserted in the holding member 248 and bearing on the spring retainer 249. The spring retainer 249 is pushed leftward by a male screw 252 screwed from the right side through a threaded bore 251 extending through the spring mount plate 245, whereby the biasing force of the spring 247 is adjusted.

The two arms 239 turn with the rod 241, and also move in the left-right direction with the rod 241 relative to the support 233, whereby the movable clamp member 234 is movable between a holding position (see the solid-line position in FIG. 6) where the member 234 holds the heat exchanger 1 in a horizontal state along with the fixed clamp members 224 and a release position (see the chain-line position in FIG. 6) where the member 234 releases the heat exchanger 1. Incidentally, when the movable clamp member 234 is in the holding position, the pin 244 is in a vertical position, consequently rendering the movable clamp member 234 free to rotate about a vertical axis. Further when the movable clamp member 234 is in the release position, the recessed portions 238 of the clamp portions 236 have their openings directed toward an obliquely upward direction. Provided between each arm 239 and the corresponding support 233 is a torsion coil spring 253 (biasing means) capable of biasing the arm 239 counterclockwise in FIG. 6 when the movable clamp member 234 is in the holding position, or biasing the arm 239 clockwise in FIG. 6 when the movable clamp member 234 is in the release position.

The high-pressure air supply device 41 is provided with an air supply hose (not shown) having at its outer end a connector connectable to the inlet pipe 7 or outlet pipe 8 of the heat exchanger 1. The air supply hose extends into the first chamber 202 through a partition wall separating the first chamber 202 from the second chamber 203.

The illuminator 42 comprises a casing 260 having an opening at its upper side, a plurality of fluorescent lamps 261 (light sources) arranged inside the casing 260, a light diffuser 262 closing the upper-side opening of the casing 260 for evenly diffusing the light from the lamps 261 to provide planar illumination, and a reflector 263 disposed under the fluorescent lamps 261 inside the casing 260 for reflecting the light emitted by the lamps 261 upward to provide intense upward light (see FIG. 6). The number of fluorescent lamps 261 is preferably smaller in view of cost, the quantity of heat generated, etc. Even if the number of lamps 261 is small, the light diffuser 262 and the reflector 263 function to provide planar illumination, affording intense upward light.

The light projected from the illuminator 42 and passed through the air passing clearances 5 between the respective adjacent pairs of heat exchange tubes 4 of the heat exchanger 1 held by the holder 40 is reflected at the reflector 43 toward the CCD cameras 44. Since the CCD cameras 44 have a definite angle of view, the portions of light passing through the portions of the clearances 5 close to the headers 2, 3 can not be reflected at the reflector 43 toward the cameras 44. To prevent this, auxiliary reflectors 254 are arranged on the left and right sides of the reflector 43 inside the fourth chamber 205 (see FIG. 9). A plurality of CCD cameras 44 are arranged upward or downward, and in the left-right direction.

Using the first embodiment of pressure resistance inspecting apparatus, the heat exchanger 1 is inspected for pressure resistance by a first method as will be described below.

First, the vertically movable door 207 is raised to open the inlet-outlet opening 206. As this time, the movable clamp member 234 of the holder 40 is in the release position. One of the headers, 2, of the heat exchanger 1 is then fitted into the recessed portions 225 of fixed clamp members 224 of the first clamp device 220 of the holder 40. The other header 3 of the heat exchanger 1 is fitted into the recessed portions 238 of the movable clamp member 234 of the second clamp device 221. Subsequently, the movable clamp member 234 is pushed down to the holding position. At this time, the heat exchanger 1 is firmly fixed by the clamp members 224, 234 by the biasing force of the compression coil spring 247. One of the inlet pipe 7 and the outlet pipe 8 is closed, and the connector at the outer end of the air supply hose of the air supply device 41 is then attached to the other pipe. The movable door 207 is thereafter lowered to close the inlet-outlet opening 206 to start a pressure resistance inspection by the manipulation-display device 46.

The heat exchanger 1 is irradiated with light from below by the illuminator 42, and an image reflected at the reflector 43 is captured by each of the CCD cameras 44 as a monochromatic image. The image signal obtained by the cameras 44 is fed to the image processor 45. The processor 45 divides the monochromatic image captured by the cameras 44 into dots (pixels), converts the luminance data of the dots into binary data items of white areas and black areas with reference to a predetermined threshold value, counts up the number of black areas of the monochromatic image and stores the number of black areas. The number of black areas obtained for the heat exchanger 1 before the application of pressure to its interior is smaller since a larger quantity of light passes through the air passing clearances 5 between the respective adjacent pairs of heat exchange tubes 4.

High-pressure air is then supplied to the interior of the heat exchanger from the device 41 to pressurize the interior of the exchanger 1, the number of binary data items of black areas in each of the images obtained is counted, and the number of black area is stored in the same manner as above.

Figure 10:
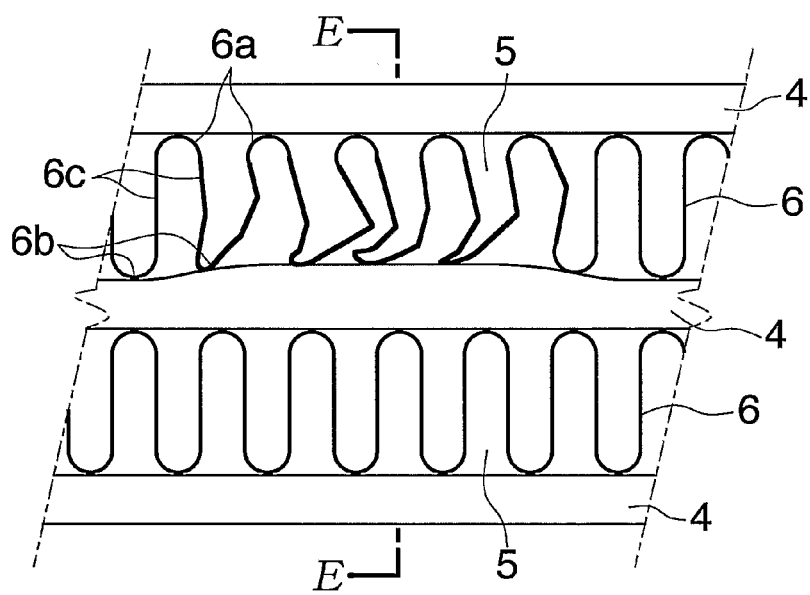
FIG. 10 is an enlarged front view corresponding to a portion of FIG. 1 and showing inside joints of the flat heat exchange tube as broken by the application of pressure to the interior of the heat exchanger by a first method using the first embodiment of pressure resistance inspecting apparatus.
Figure 11:
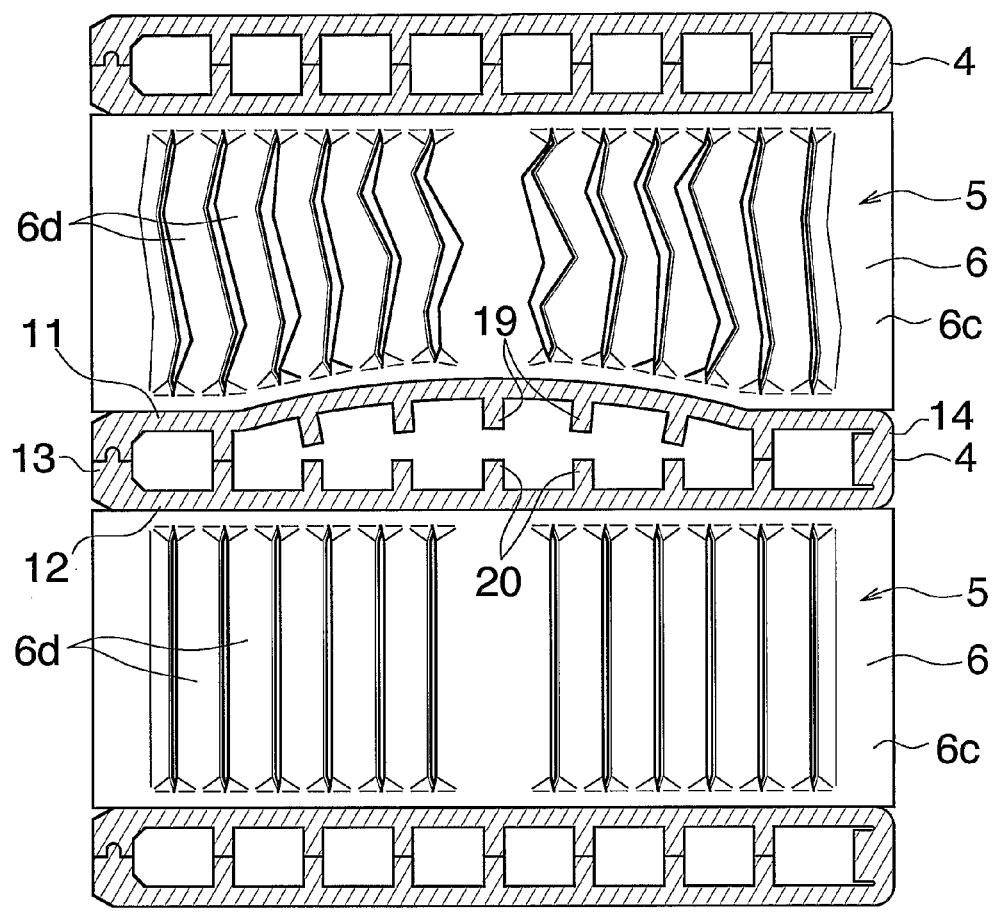
FIG. 11 is an enlarged view in section taken along the line E-E in FIG. 10.

When brazing joints between the reinforcing wall ridges 19, 20 of the heat exchanger 1 have brazing faults or are insufficient in joint strength, the pressure applied to the interior of the exchanger 1 breaks faulty inside joints of the reinforcing wall ridges 19, 20 to create a relatively large clearance between the ridges 19, 20, greatly inflating the tube 4 and deforming the corrugated fin 6 disposed in the air passing clearance 5 as shown in FIGS. 10 and 11. This reduces the quantity of light passing through the air passing clearance 5 and greatly increases the number of black areas counted up by the image processor 45 as compared with the number of black areas before the pressurization. In this case, the image processor 45 compares the number of black areas after the application of pressure with the number of black areas before the pressure application, and if the increase in the number of black areas after the pressure application is not smaller than a predetermined threshold value, the processor interprets this result as indicating an unacceptable product which is insufficient in pressure resistance and shows the result of inspection on the manipulation-display device 46.

Conversely, if the brazing joints between the reinforcing ridges 19, 20 of the heat exchanger 1 are free from any brazing faults and when the brazing joints have a sufficiently great strength, the application of pressure to the interior of the exchanger 1 causes almost no bulging of the heat exchange tubes 4 or no deformation of the corrugated fins 6, and the quantity of light passing through the clearances 5 remains almost unaltered as compared with the corresponding quantity before the pressurization. As a result, the number of black areas counted up by the image processor 45 remains almost unincreased from the number of black areas before the pressurization, and the increase in the number of black areas resulting from the pressurization is less than the predetermined threshold value. In this case, the processor 45 interprets the result as indicating an acceptable product having high pressure resistance, and displays the result on the manipulation-display device 46.

In the event of occurrence of the deformation of the heat exchanger 1 in its entirety or a shift thereof when the interior of the exchanger 1 is pressurized, the movable clamp member 234 moves toward or away from the fixed clamp members 224 and is biased toward the fixed clamp members 224 by the compression coil spring 247, whereby the deformation, deterioration or wear of the clamp members 224, 234 can be inhibited. The movable clamp member 234 is rotatable about a vertical axis when in the holding position, and the movable clamp member 234 is movable longitudinally of the header 3 of the heat exchanger 1 in addition to being movable toward or away from the fixed clamp members 224. This suppresses the shift of the heat exchanger 1 from a reference position thereof for inspection.

Although CCD cameras 44 are used as the image pickup means according to the above first embodiment, these means are not limitative; for example, a line sensor may be used. In this case, means is provided for moving the line sensor and the heat exchanger 1 relative to each other so as to capture an overall image of the exchanger 1 reflected from the reflector. Further in place of CCD cameras 44, light receiving elements of transmission sensors are usable as the image pickup means.

In this case, the light projecting elements of the transmission sensors serve as the irradiating means. When the transmission sensors are used, the sensor device and the heat exchanger 1 are moved relative to each other so as to capture an overall image of the exchanger 1 reflected from the reflector.

The holding means used in the foregoing first embodiment comprises a first clamp device 220 having fixed clamp members 224 and a second clamp device 221 having a movable clamp member 234, whereas a device may alternatively be used which comprises a first clamp assembly having a movable clamp member for holding one of the headers, 2, of the heat exchanger 1, and a second clamp assembly having a movable clamp member for holding the other header 3, the movable clamp member of one of the assemblies being movable toward or away from the movable clamp member of the other assembly and being biased by biasing means toward the movable clamp member of the other assembly, the first and second clamp assemblies being at least three in total number. In this case, the movable clamp member of each clamp assembly is rotatable about a vertical axis and movable longitudinally of the headers 2, 3 of the exchanger 1 when holding the heat exchanger 1.

With the pressure resistance inspecting apparatus according to the first embodiment and shown in FIG. 4, the image processor 45, which has the foregoing function, may further have the function of continuously or intermittently counting the number of black areas after the pressurization of the interior of the heat exchanger 1 with the high-pressure air supplied to the exchanger 1 by the air supply device 41 and storing the number, the function of determining the pressure resistance of the heat exchanger 1 based on the continuous variations or intermittent variations in the number of black areas before the pressurization and the number of black areas after the pressurization and feeding the result to the manipulation-display device 46, and the function of discontinuing the supply of high-pressure air to the interior of the heat exchanger 1 by the air supply device 41 in the event of the number of black areas increasing abnormally after the pressurization.

A second method will be described below of inspecting the heat exchanger 1 for pressure resistance using the pressure resistance inspecting apparatus having the image processor 45 described.

Figure 12:
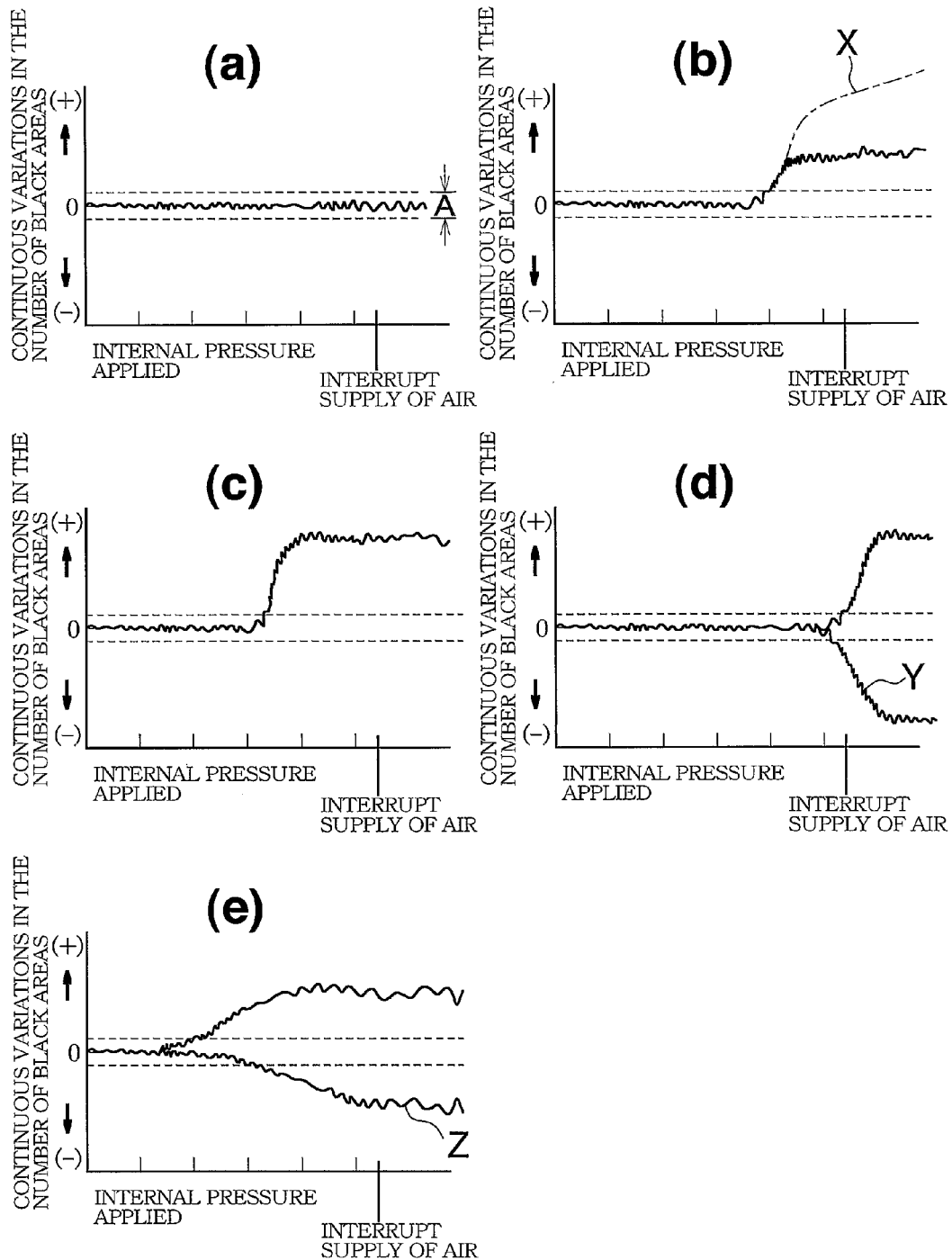
FIG. 12 includes graphs showing the relationship between the pressure applied to the interior of the heat exchanger in various states and the continuous variations in the number of black areas, for use in a second method using the apparatus of first embodiment.

The second method judges whether the heat exchanger 1 is acceptable or not in the same manner as the first method described. Furthermore, the heat exchanger 1 can be checked for various states by the second method with reference to FIG. 12 showing the relationship between the internal pressure applied and the continuous variations in the number of black areas involved in various states of the heat exchanger 1 as will be described below.

FIG. 12(a) shows a case wherein all the reinforcing walls 15 of the heat exchange tube 4 are free from faults in the brazing joints between the reinforcing wall ridges 19, 20. In this case, variations in the number of black areas are within a predetermined range A, and the increase (variation) in the number of black area is less than a predetermined threshold value.

FIG. 12(b) shows a case involving faults in a small number of reinforcing walls 15, for example, faults occurring in the brazing joint between the ridges 19, 20 of one reinforcing wall 15 and no faults occurring in the brazing joints between the ridges 19, 20 of the other reinforcing walls 15, or a case involving faults occurring in the brazing joints between the ridges 19, 20 of at least two reinforcing walls 15 which are positioned between a plurality of reinforcing walls 15 having no faults in the joints between their ridges 19, 20. Since the reduction in the pressure resistance is not great in this case, heat exchange tubes 4 and corrugated fins 6 deform at relatively high internal pressure applied to result in a rapid increase in the number of black areas, and the number of black areas increases beyond the threshold value, indicating that the product is unacceptable. In the event of faulty brazing occurring between the ridges 19, 20 of at least two reinforcing walls 15 which are positioned between a plurality of reinforcing walls 15 having no faults in the joints between their ridges 19, 20, a break is likely to occur in the brazing joint or joints between the ridges 19, 20 of the wall or walls 15 as positioned between the faulty two reinforcing walls 15, hence a markedly great increase in the number of black areas as indicated in a chain line X in FIG. 12(b).

FIG. 12(c) shows a case involving faults occurring in the brazing joints between the ridges 19, 20 of many reinforcing walls 15. Since this case involves a more marked reduction in the pressure resistance than is shown in FIG. 12(b), heat exchange tubes 4 and corrugated fins 6 greatly deform at a lower internal pressure than is the case with FIG. 12(b), entailing a great increase in the number of black areas. The increase in the number of black areas therefore exceeds the threshold value in a shorter period of time than is the case with FIG. 12(b) to indicate an unacceptable product. The increase in the number of black areas in this case is comparable to the corresponding number indicated in the chain line X in FIG. 12(b).

FIG. 12(d) shows a case of brazing joints of insufficient strength, for example, due to faulty application of flux for brazing although each of all the reinforcing walls 15 has its ridges 19, 20 brazed to each other. The increase in the number of black areas remains not higher than the threshold value even when the internal pressure applied is higher than in FIG. 12(c), whereas the brazing joints between the ridges 19, 20 of many reinforcing walls 15 break upon the internal pressure increasing to a specified level, causing heat exchange tubes 4 and corrugated fins 6 to deform markedly and permitting a pronounced increase in the number of black areas to exceeds the threshold value, hence the judgment of an unacceptable product. Since tubes 4 and fins 6 deform to excess in this case, tubes 4 will shift to result in the likelihood that the dots of the portion corresponding to the tube 4 in the range of image area which were black areas will become white areas, and the number of black areas will decrease as indicated in a curve Y in FIG. 12(d).

FIG. 12(e) shows a case wherein the heat exchanger 1 is made as corrected with an objectionable force applied to deformed headers 2, 3, heat exchange tubes 4 and fins 6 although no brazing faults occurred between the ridges 19, 10 of any reinforcing wall 15 of the tubes 4. When the internal pressure increases in this case, the heat exchanger 1 deforms in its entirety at a relatively low pressure, increasing the number of black areas and permitting the increase in the number of black areas to exceed the threshold valve to indicate an unacceptable product. Since heat exchange tubes 4 and corrugated fins deform to excess in this case, tubes 4 will shift to result in the likelihood that the dots of the portion corresponding to the tube 4 in the range of image area which were black areas will become white areas, and the number of black areas will decrease as indicated in a curve Z in FIG. 12(e).

The kind of faults in the heat exchanger 1 can be identified with reference to FIG. 12, (a) to (e) showing the relationship between the internal pressure applied and the continuous variations in the number of black area, whereby a countermeasure to be taken can be worked out.

In the second method described, the number of black areas can be counted intermittently by the image processor 45 after the start of pressurization.

With the pressure resistance inspecting apparatus of the first embodiment shown in FIG. 4, the image processor 45 performs a mode of inspection by dividing a monochromatic image captured by each of the CCD cameras 44 into dots (pixels), converting luminance data as to the dots into binary data items of white areas and black areas with reference to a predetermined threshold value to extract a pattern of white areas and black areas in the monochromatic image, repeating the same procedure as above after the pressurization of the interior of the heat exchanger 1 by the air supply device 41 to obtain a pattern after the pressurization, comparing the pattern before the pressurization with the pattern after the pressurization, judging the pressure resistance of the heat exchanger 1 with reference to the two patterns before and after the pressurization and feeding the result of judgment to the manipulation-display device 46.

A third method will be described below of inspecting heat exchangers 1 for pressure resistance using the pressure resistance inspecting apparatus having the image processor 45 described.

First, the heat exchanger 1 is set in the inspecting apparatus in the same manner as in the first method.

The heat exchanger 1 is irradiated with light from below by the illuminator 42, and images of the exchanger as reflected at the reflector 43 are captured by the CCD cameras 44 as a monochromatic image. Each of the cameras 44 feeds an image signal to the image processor 45. The processor 45 divides the monochromatic image captured by the CCD camera 44 into dots (pixels), converts luminance data as to the dots into binary data items of white areas and black areas with reference to a predetermined threshold value, extracts a pattern of white areas and black areas in the range of image captured and stores the pattern.

High-pressure air is then supplied by the air supply device 41 to the interior of the heat exchanger 1 to pressurize the interior to a specified level, and the same procedure as above is repeated to extract a pattern of white areas and black areas in the range of image captured.

When brazing joints between the reinforcing wall ridges 19, 20 of the heat exchanger 1 have faults or are insufficient in joint strength, the pressure applied to the interior of the exchanger 1 breaks faulty inside joints of the reinforcing wall ridges 19, 20 to create a relatively large clearance between the ridges 19, 20, greatly inflating the tube 4 and deforming the corrugated fin 6 disposed in the air passing clearance 5. This reduces the quantity of light passing through the air passing clearance 5, and the pattern to be extracted by the processor 45 will greatly differ from the pattern obtained before the pressurization. In this case, the image processor 45 compares the pattern after the pressurization with the pattern before the pressurization, and if the variation in the pattern resulting from the pressurization is not smaller than a threshold value, the processor 45 interprets this result as indicating that the product is insufficient in pressure resistance and therefore unacceptable. The processor shows the result of judgment on the manipulation-display device 46.

Conversely, if the brazing joints between the reinforcing ridges 19, 20 of the heat exchanger 1 are free from any brazing faults and have a sufficiently great strength, the application of pressure causes no break in the inside joints between the reinforcing wall ridges 19, 20 while slightly deforming heat exchange tubes 4 and corrugated fins 6. The deformation ceases to be less than a predetermined degree. At this time, the pattern after the pressurization remains almost unaltered from the pattern before the pressurization. The image processor 45 then interprets the result as indicating an acceptable product of high pressure resistance, and shows the result of judgment on the display device 46.

In the event of heat exchange tubes 4 and corrugated fins 6 deforming with a break occurring in the inside end-to-end joint between the reinforcing wall ridges 19, 20, and also in the event of heat exchange tubes 4 and corrugated fins 6 deforming without a break in the inside joint, it is likely that the pattern after the pressurization will alter owing to the deformation and distortion of the heat exchanger 1 in its entirety or to a flicker. However, the deformation of tubes 4 and fins 6 involving a break in the inside joint, the deformation of tubes 4 and fins 6 without a break in the joint, and the deformation and distortion of the entire exchanger 1 or a flicker produce different alterations in the pattern, so that the image processor discriminates between the two cases, i.e., the deformation of tubes 4 and fins 6, and the deformation and distortion of the entire exchanger 1 or a flicker, with reference to the pattern before the pressurization and the pattern after the pressurization.

In the case where tubes 4 and fins 6 only deform without a break in the joint between the reinforcing wall ridges 19, 20, the pressurization produces little or no alteration in the pattern before the pressurization. The image processor 45 then interprets this result as indicating that the product has high pressure resistance and is acceptable and shows the result on the display 46.

With the pressure resistance inspecting apparatus of the first embodiment shown in FIG. 4, the image processor 45 operates in another mode, that is, the processor 45 divides a monochromatic image captured by the CCD cameras 44 into dots (pixels), converts luminance data as to the dots into binary data items of white areas and black areas with reference to a predetermined threshold value by gray image processing, extracts a pattern of white areas and black areas in the monochromatic image, repeats the same procedure after the pressurization of the interior of the heat exchanger 1 by the air supply device 41 to obtain a pattern after the pressurization, compares the pattern before the pressurization with the pattern after the pressurization, judges the pressure resistance of the heat exchanger 1 based on the pattern before the pressurization and on continuous variations or intermittent variations in the pattern after the pressurization, and feeds the result of judgment to the manipulation-display device 46. Furthermore, the image processor 45 may show on the manipulation-display device 46 the internal pressure causing the pattern to start to vary after the start of pressurization and the internal pressure at the time when the pattern ceases to alter. Upon the pattern altering abnormally after the start of pressurization, the image processor 45 may cease to supply high-pressure air to the interior of the heat exchanger by the air supply device 41.

A fourth method will be described below of inspecting the heat exchanger 1 for pressure resistance using the pressure resistance inspecting apparatus having the image processor 45 described.

The fourth method judges whether the heat exchanger 1 is acceptable or unacceptable in the same manner as the third method described. The fourth method is further capable of checking the heat exchanger 1 as internally pressurized to discriminate between two cases, i.e., the occurrence of deformation of heat exchange tubes 4 and corrugated fins 6 and the occurrence of deformation and distortion of the entire heat exchanger 1 involving a flicker.

Stated more specifically, in the case where heat exchange tubes 4 and corrugated fins 6 deform with a break occurring in the inside end-to-end joint between the reinforcing wall ridges 19, 20, and also in the case where heat exchange tubes 4 and corrugated fins 6 deform without a break in the inside joint, it is likely that the pattern after the pressurization will alter owing to the deformation and distortion of the heat exchanger 1 in its entirety or to a flicker. However, the deformation of tubes 4 and fins 6 involving a break in the inside joint, the deformation of tubes 4 and fins 6 without a break in the joint, and the formation and distortion of the entire exchanger 1 or a flicker produce different alterations in the pattern, so that the image processor discriminates between the two cases, i.e., the deformation of tubes 4 and fins 6, and the deformation and distortion of entire exchanger 1 or flicker, based on the pattern before the pressurization and on continuous variations and intermittent variations in the pattern after the pressurization.

Figure 14:
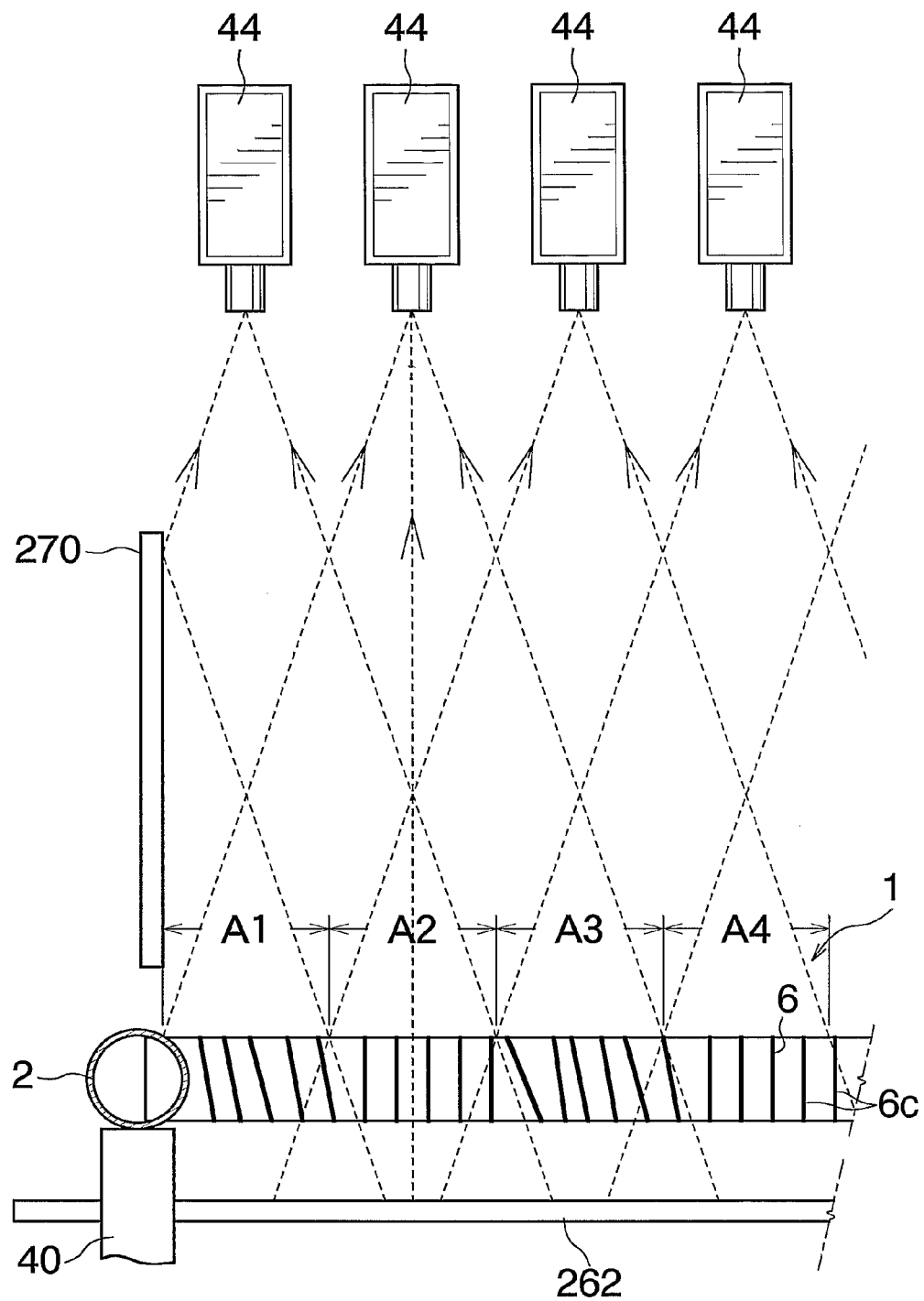
FIG. 14 is an enlarged fragmentary view of FIG. 13.

FIGS. 13 and 14 schematically show the construction of a second embodiment of pressure resistance inspecting apparatus of the invention for heat exchangers.

This embodiment includes CCD cameras 44 having an angle of view and arranged with their optical axes positioned in parallel and directed vertically so that their image capturing ranges lap over one another. An image of a heat exchanger 1, as irradiated with light by an illuminator 42 from below, is captured as a monochromatic image by each of the CCD cameras 44 from above, and the resulting image signal is fed to an image processor 45.

With reference to FIG. 14, images of portions A2, A3, A4 of the heat exchanger 1 other than the portions A1 thereof close to opposite headers 2, 3 are captured by adjacent cameras 44, i.e., three cameras 44 in this embodiment, from different directions, i.e., three directions in this embodiment. For example, images of the portion A2 are captured by the second camera 44 from the left in FIG. 14 from immediately thereabove, by the camera 44 at the left end from obliquely leftwardly above, and by the third camera 44 from the left from obliquely rightwardly above. Further images of the portion A1 of the heat exchanger 1 close to each of the headers 2, 3 are captured by the camera 44 at the corresponding end and by the camera 44 adjacent to this camera 44 from a plurality of directions, i.e., three directions in the present embodiment. Stated more specifically, an image of the portion A1 is directly captured by the camera 44 at the left end from immediately above, and an image of the portion A1 as reflected at a reflector plate 270 is captured by the camera 44 at the left end and is thereby captured from obliquely leftwardly above. An image of the portion A1 is further captured by the second camera 22 from the left from obliquely rightwardly above. Accordingly, images of each of the portions A1, A2, A3, A4 of the heat exchanger 1 are captured by CCD cameras 44 from a plurality of directions, i.e., from three directions in the present embodiment, and a plurality of, i.e., three, images are obtained for each of the portions A1 to A4.

The image processor 45 divides images, i.e., three monochromatic images, of each of the portions A1 to A4 of the heat exchanger 1 captured by all CCD cameras 44 from a plurality of directions, i.e., three directions, into a plurality of dots (pixels), converts luminance data as to the dots of each image into binary data items of white areas and black areas with reference to a predetermined reference value, and counts the number of black areas. The image processor 45 further calculates by addition the sum of the numbers of black areas of three monochromatic images of each of the portions A1 to A4 of the heat exchanger 1 and stores the total number of black areas. The image processor 45 further compares the result of calculation of the numbers of black areas in the state before the pressurization of interior of the heat exchanger 1 by the supply of high-pressure air thereto by the air supply device 41, with the result of calculation of the numbers of black areas in the state after the pressurization, judges the pressure resistance of the heat exchanger 1 based on the increase in the number of black areas due to the pressurization, and feeds the result of judgment to a manipulation-display device 45.

With the exception of the above feature, the second embodiment is the same as the first embodiment.

Using the apparatus of the second embodiment, the heat exchanger is inspected for pressure resistance by a method which is similar to the first method and the second method to be practiced using the apparatus of the first embodiment. However, the number of black areas for each of the portions A1 to A4 is counted by the apparatus of the second embodiment by calculating by addition the sum of numbers of black areas of three monochromatic images captured for each of the portions A1 to A4. The first method uses as a reference for judgment the increase in the total number of black areas in all monochromatic images after the pressurization from the total number of black areas in all monochromatic images before the pressurization. Further the second method uses as a reference for judgment continuous variations or intermittent variations in the total number of black areas in all monochromatic images after the pressurization, from the total number of black areas in all monochromatic images before the pressurization.

These methods have the following advantage. Three images of each of portions A1, A2, A3, A4 of the heat exchanger 1 are captured by the CCD cameras 44 from a plurality of directions, i.e., three directions, so that even if the corrugated fin 6 disposed in an air passing clearance 5 is deformed to such an extent that the passage of air therethrough will not be thereby affected, the heat exchanger 1 can be inspected for pressure resistance easily and accurately. Stated more specifically, even if the corrugated fin 6 in the portions A1 to A4 of the heat exchanger 1 includes inclined connecting portions 6c as shown in FIG. 14, the inclined portions are unlikely to greatly increase the resistance to the passage of air and entail seriously impaired heat exchange performance. However, suppose images of the portions A1 to A4 are captured by the CCD cameras 44 from one direction. For example, suppose an image of the portion A1 of FIG. 14 is captured directly by the camera 44 at the left end from immediately above or by the second camera 44 from the left, only from obliquely rightwardly above; or suppose an image of the portion A2 is captured by the camera 44 at the left end only from obliquely leftwardly above or by the third camera 44 from the left, only from obliquely rightwardly above; or suppose an image of the portion A3 is captured by the third camera 44 from the left, only from immediately above or by the fourth camera 44 from the left, only from obliquely rightwardly above; or suppose an image of the portion A4 is captured by the third camera 44 from the left, only from obliquely leftwardly above. In these cases, an insufficient quantity of light passes through the clearances between adjacent connecting portions 6c of the corrugated fin 6 disposed in the air passing clearance 5 to produce an excessive number of black areas in each monochromatic image. It is then likely that the product will be interpreted as being low in air passing performance and unacceptable before the pressurization. On the other hand, in the case where three images of each of the portions A1 to A4 are captured from a plurality of directions, i.e., three directions, the number of binary data items of black areas in one or two of the monochromatic images of each exchanger portion will be excessive, but at least one monochromatic image of the portion is lesser in the number of binary data items of black areas. For example, the monochromatic images of the portion A3 of FIG. 14 captured with the third and fourth cameras 44 from the left provide an excessive number of black areas by conversion to binary data items, whereas the monochromatic image captured with the second camera 44 from the left is lesser in the number of binary data items of black areas. Accordingly, the likelihood of judging an acceptable exchanger as being unacceptable can be obviated by calculating the total number of binary data items of black areas in a plurality of images, i.e., three monochromatic images, of each of the portions A1, A2, A3, A4 and judging the air passing performance based on the total number of black areas.

While the pressure resistance inspecting apparatus is used for inspecting heat exchangers 1 for pressure resistance according to the second embodiment described, whether the heat exchanger 1 is to be inspected for pressure resistance can be determined based on the calculated number of black areas of the images of each of the portions A1 to A4 of the heat exchanger 1. If the corrugated fine 6 is found deformed or when the flux used for brazing the flat heat exchange tube 4 to corrugated fins 6 is found remaining in a large amount to block the air passing clearance 5 before pressurization, the monochromatic images provide a greatly increased total number of black areas, which indicates that the exchanger 1 is unacceptable before the inspection of pressure resistance, thus obviating the need for the inspection.

Furthermore, individual corrugated fins can be checked for state in the same manner as above before they are incorporated into a heat exchanger.

Figure 15:
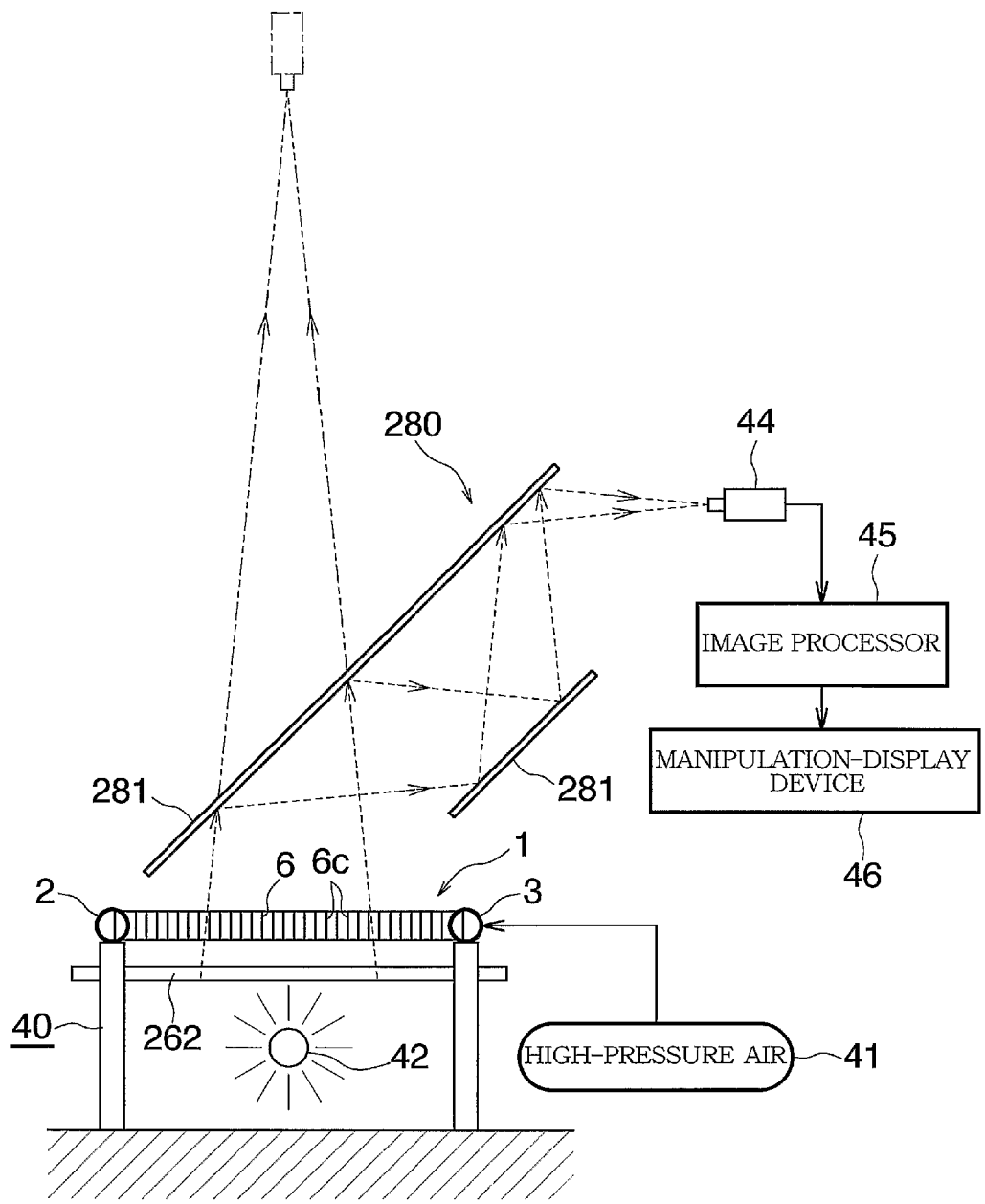
FIG. 15 is a diagram schematically showing the construction of a third embodiment of pressure resistance inspecting apparatus of the invention for heat exchangers.

FIG. 15 schematically shows the construction of a third embodiment of apparatus of the invention for inspecting heat exchangers for pressure resistance.

The third embodiment has above a heat exchanger 1 held on a holder 40 reflecting means 280 for reflecting light from below laterally, i.e., rightward in this case, and CCD cameras 44 for capturing images reflected at the reflecting means 280.

The reflecting means 280 comprises a plurality of, i.e., two, reflector plates 281 each having a planar reflective surface and to be irradiated by an illuminator 42 from below for reflecting the light passing between respective adjacent pairs of connecting portions 6c of a corrugated fin 6 disposed in each air passing clearance of the heat exchanger 1 at least twice, i.e., three times in the illustrated case, to guide the light to the cameras 44.

The third embodiment otherwise has the same construction as the first embodiment described.

Figure 16:
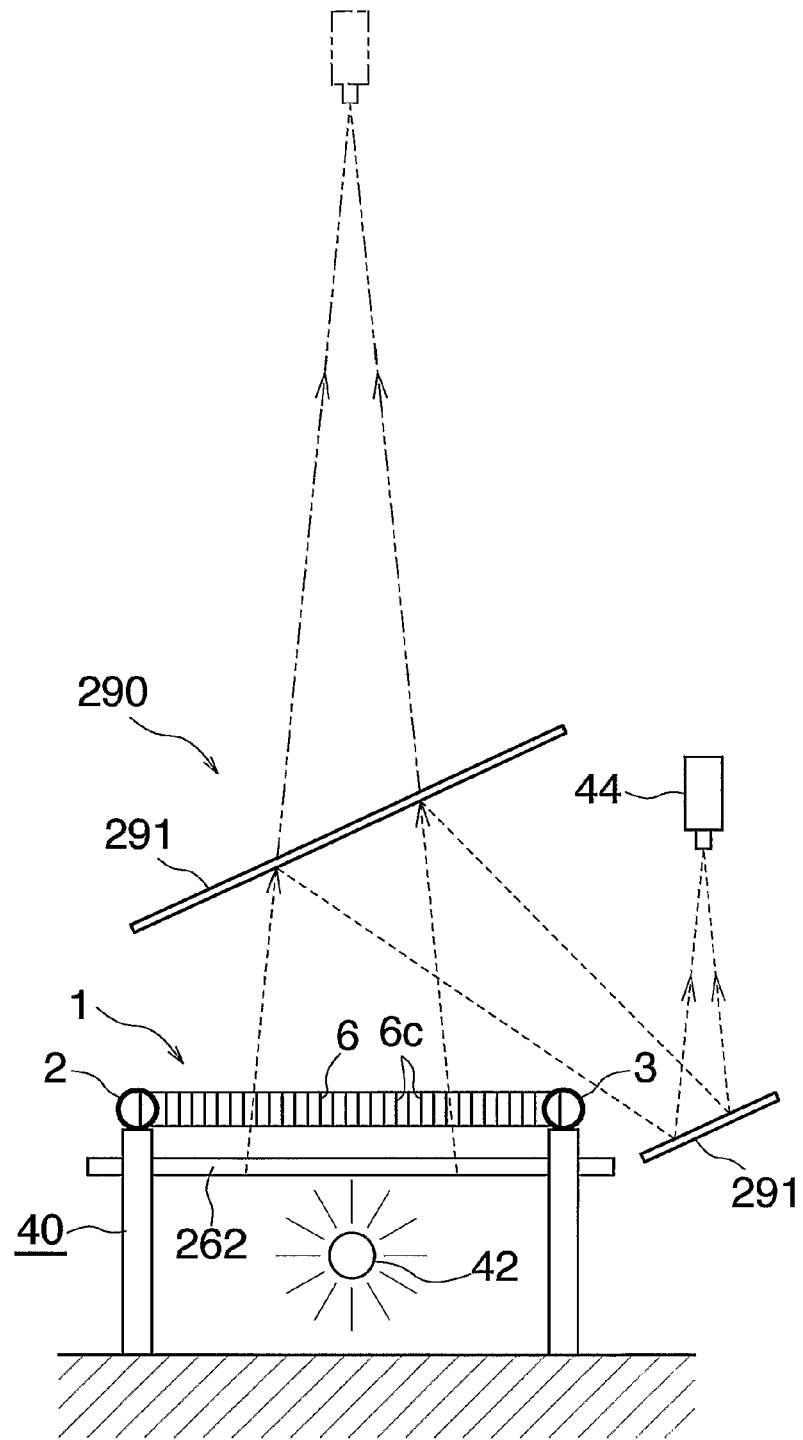
FIG. 16 is a diagram schematically showing the construction of a fourth embodiment of pressure resistance inspecting apparatus of the invention for heat exchangers.

FIG. 16 schematically shows the construction of a fourth embodiment of apparatus of the invention for inspecting heat exchangers for pressure resistance.

The fourth embodiment has reflecting means 290 for reflecting light from below a heat exchanger 1 upward, and CCD cameras 44 for capturing images, reflected at the reflecting means 290, from above.

The reflecting means 290 comprises a plurality of, i.e., two, reflector plates 291 each having a planar reflective surface and to be irradiated by an illuminator 42 from below for reflecting the light passing between respective adjacent pairs of connecting portions 6c of a corrugated fin 6 disposed in each air passing clearance of the heat exchanger 1 at least twice, i.e., three times in the illustrated case, to guide the light to the cameras 44. Although not shown, an image processor is connected to the cameras 44 and has connected thereto a manipulation-display device.

The fourth embodiment otherwise has the same construction as the first embodiment described.

Figure 17:
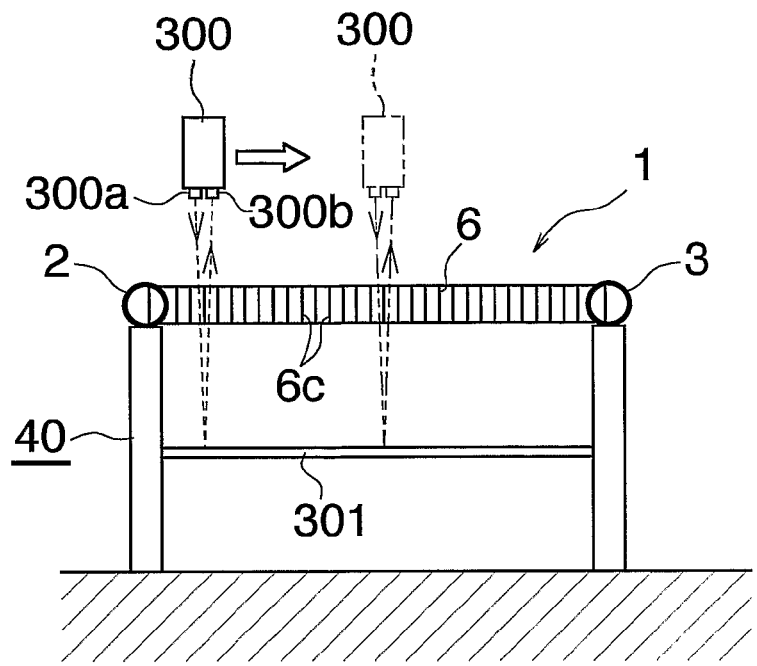
FIG. 17 is a diagram schematically showing the construction of a fifth embodiment of pressure resistance inspecting apparatus of the invention for heat exchangers.

FIG. 17 schematically shows the construction of a fifth embodiment of apparatus of the invention for inspecting heat exchangers for pressure resistance.

The fifth embodiment comprises a light projector-receiver device 300 disposed above a heat exchanger 1 as held by a holder 40, and a reflector plate 301 (reflecting means) disposed horizontally under the heat exchanger 1 held by the holder 40 for reflecting the light emitted by a projector 300a of the device 300 toward a receiver 300b of the device 300.

The projector 300a and the receiver 300b of the light projector-receiver device 300 face downward and are free to move in a horizontal plane. Although not shown, an image processor is connected to the device 300 and has a manipulation display device connected thereto. The reflector plate 301 has a flat reflective surface facing upward and having approximately the same size as the heat exchanger 1 when seen from above. The fifth embodiment otherwise has the same construction as the first embodiment described.

Figure 18:
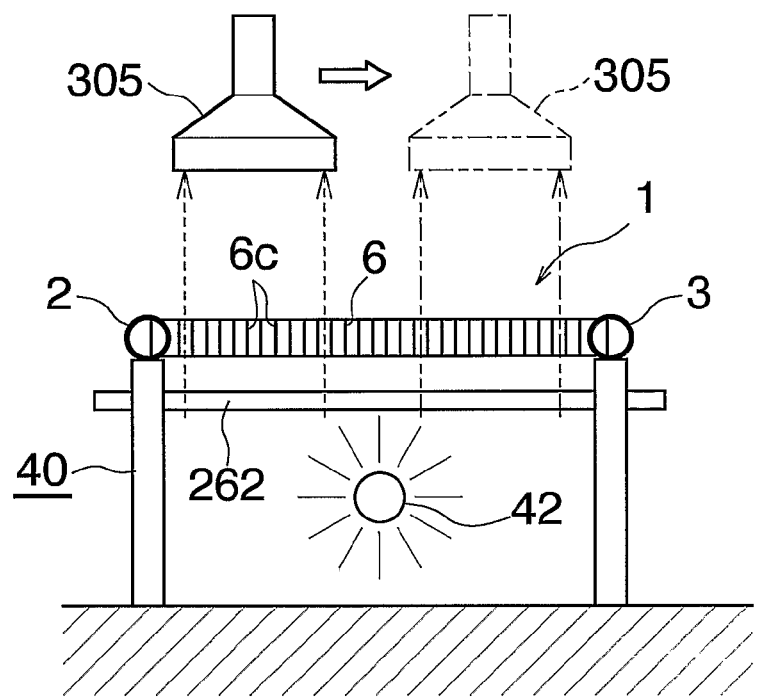
FIG. 18 is a diagram schematically showing the construction of a sixth embodiment of pressure resistance inspecting apparatus of the invention for heat exchangers.

FIG. 18 schematically shows the construction of a sixth embodiment of apparatus of the invention for inspecting heat exchangers for pressure resistance.

The sixth embodiment comprises a camera 305 (image pickup means) disposed above a heat exchanger 1 as held by a holder 40 having a lens for converging parallel rays. Useful as such a lens is, for example, a telecentric lens. The camera 305 is free to move in a horizontal plane. Although not shown, an image processor is connected to the camera 305 and has connected thereto a manipulation-display device. The sixth embodiment otherwise has the same construction as the first embodiment described.

Figure 19:
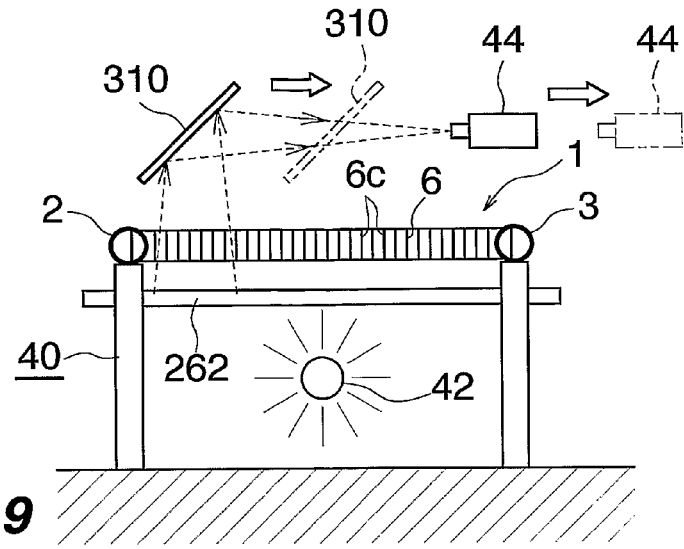
FIG. 19 is a diagram schematically showing the construction of a seventh embodiment of pressure resistance inspecting apparatus of the invention for heat exchangers.

FIG. 19 schematically shows the construction of a seventh embodiment of apparatus of the invention for inspecting heat exchangers for pressure resistance.

The seventh embodiment comprises a reflector plate 310 (reflecting means) disposed above a holder 40 and having a flat reflective surface, and CCD cameras 44 for capturing images reflected from the reflector plate 310. The reflector plate 310 and CCD cameras 44 are movable leftward or rightward in synchronism. Although not shown, an image processor is connected to the CCD cameras 44 and has a manipulation-display device connected thereto. The seventh embodiment otherwise has the same construction as the first embodiment described.

Figure 20:
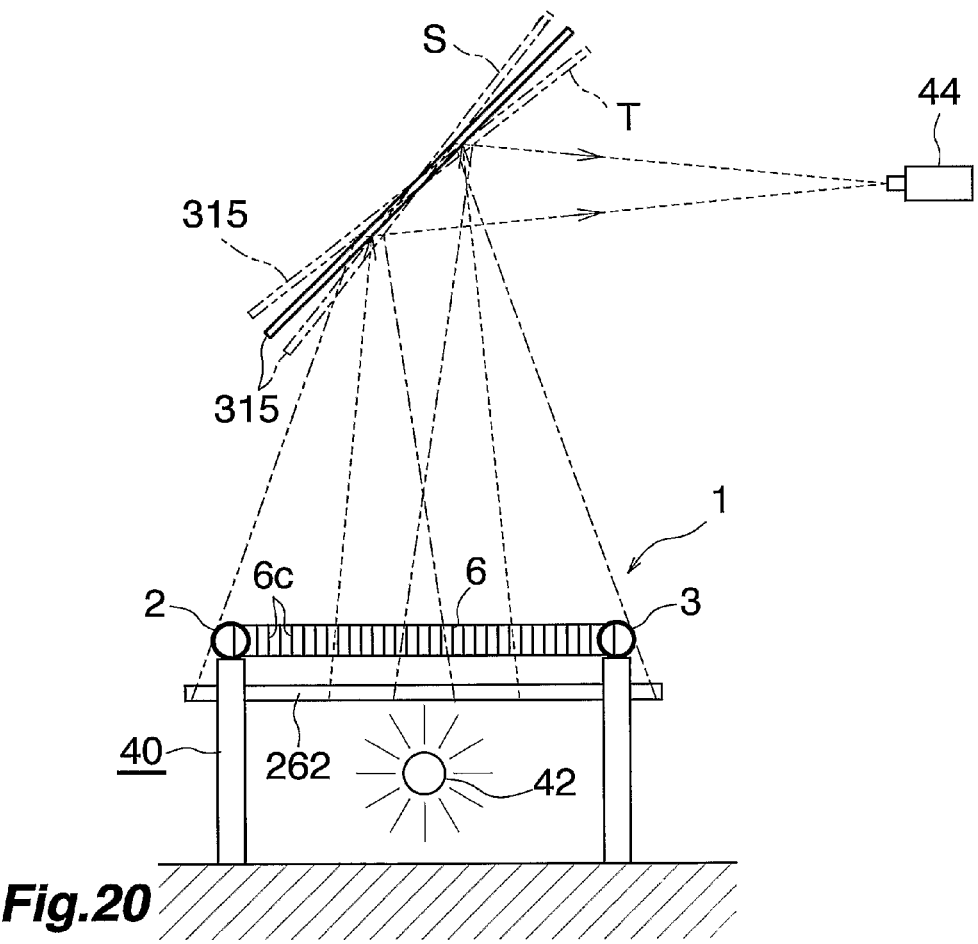
FIG. 20 is a diagram schematically showing the construction of an eighth embodiment of pressure resistance inspecting apparatus of the invention for heat exchangers.

FIG. 20 schematically shows the construction of an eighth embodiment of apparatus of the invention for inspecting heat exchangers for pressure resistance.

The eighth embodiment comprises a reflector plate 315 (reflecting means) having a flat reflective surface and disposed above a holder 40, and CCD cameras 44 for capturing images reflected at the planar reflector plate. The reflector plate 315 is free to rotate about an axis in parallel to the widthwise direction (the front side-rear side direction of the paper sheet bearing FIG. 20) of the corrugated fin 6 shown. Although not shown, an image processor is connected to the CCD cameras 44 and has a manipulation-display device connected thereto. The eighth embodiment otherwise has the same construction as the first embodiment described.

In the case of the apparatus of the eighth embodiment, images reflected at the reflector plate 315 are captured by the CCD cameras 44 at a plurality of positions, for example, at the position indicated in solid lines in FIG. 20, at the position indicated in chain lines S and at the position indicated in chain lines T, by rotating the reflector plate 315. Although reflected images of the entire heat exchanger 1 can not be captured at the solid-line position shown in FIG. 20, reflected images of the entire heat exchanger 1 can be captured at the chain-line position S or chain-line position T, whereby reflected images of the entire heat exchanger 1 can be captured. Accordingly, even if the number of CCD cameras 44 available is small, reflected images of the entire heat exchanger 1 can be captured for inspecting the exchanger 1 for pressure resistance. Since images reflected by the reflector plate 315 are captured by the cameras 44, the cameras 44 can be positioned at a relatively great distance from the exchanger 1. This enables the CCD cameras 44 to capture images of the entire exchanger 1 although having an angle of view or even if small in number, since the rays passing between respective adjacent pairs of connecting portions 6c of the corrugated fin 6 are then nearly parallel rays.

With the apparatus of the fourth to eighth embodiments, the image processor is likely to have the various functions described with reference to the first embodiment, so that heat exchangers 1 can be inspected for pressure resistance by the first to fourth methods described above.

FIGS. 21 to 25 show modifications of flat heat exchange tube serving as the refrigerant channel portion for use in the heat exchanger 1 shown in FIG. 1.

Figure 21:
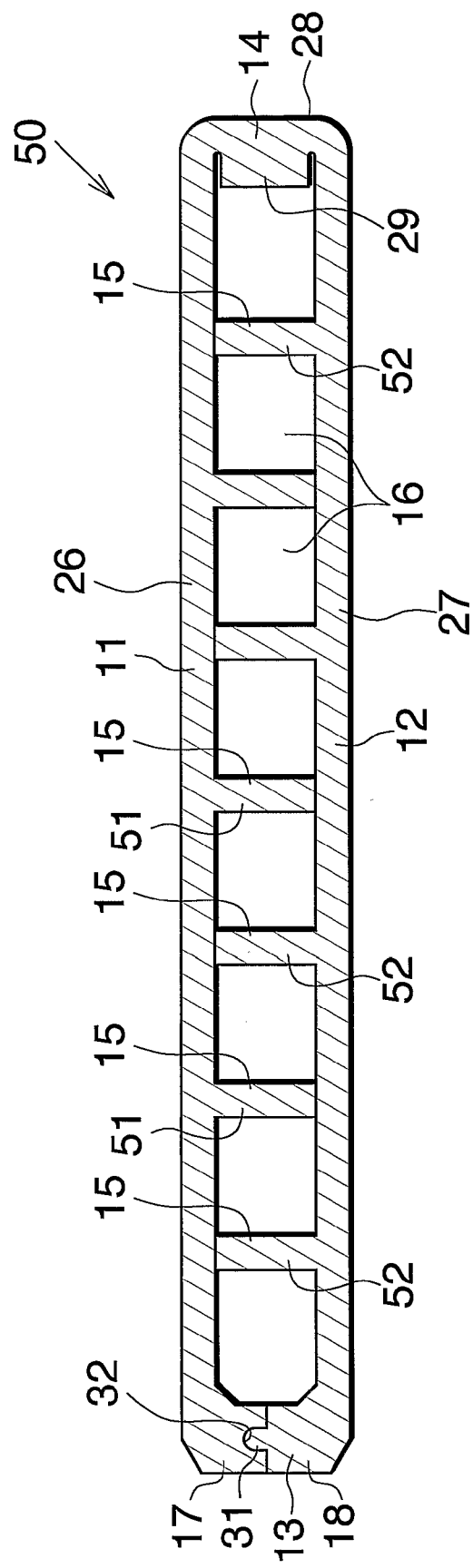
FIG. 21 is a cross sectional view showing a modified flat heat exchange tube for use in the heat exchanger of FIG. 1.
Figure 22:
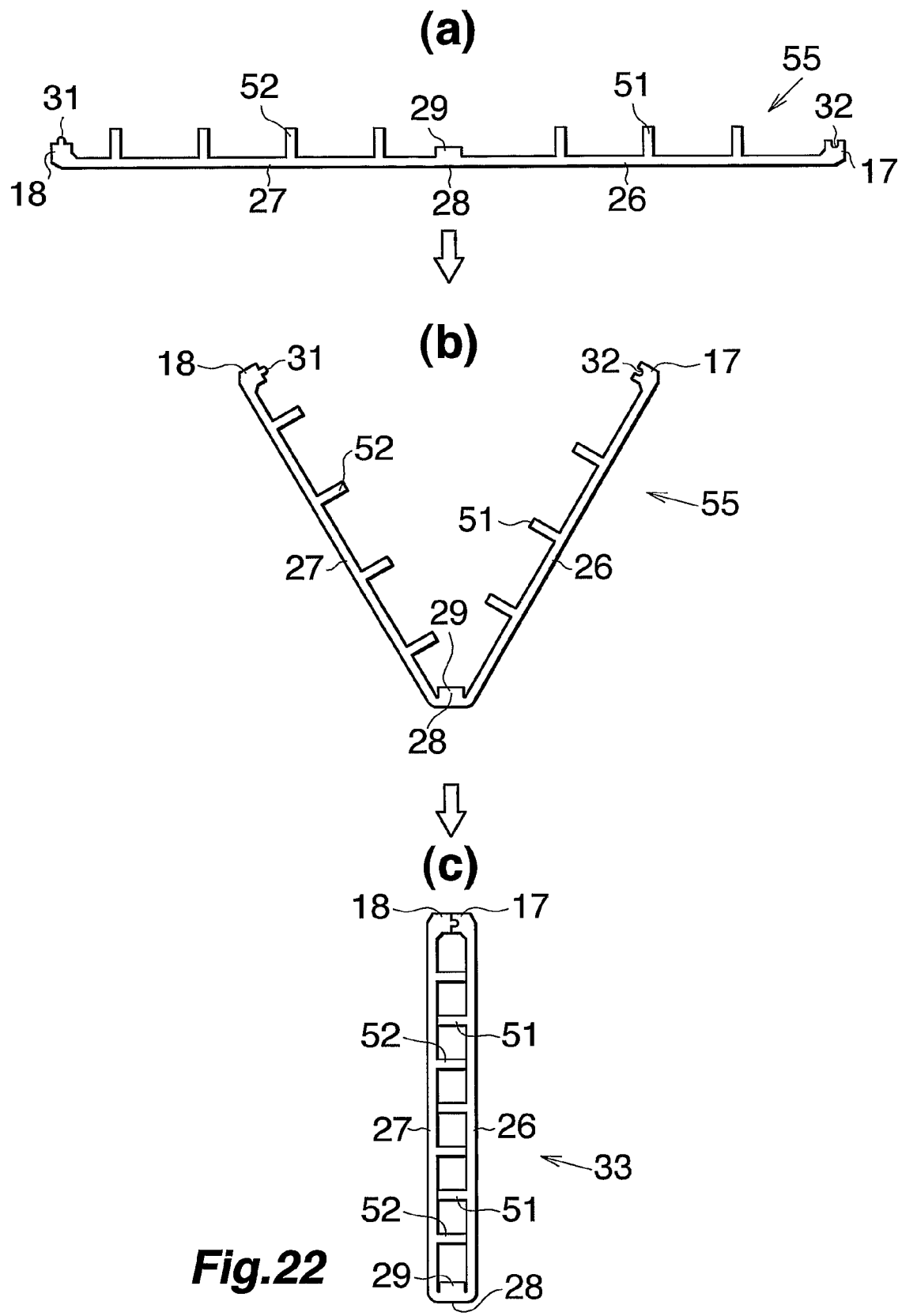
FIG. 22 is a diagram showing a process for fabricating the flat heat exchange tube of FIG. 21.

FIG. 21 shows a flat heat exchange tube 50, which has reinforcing walls 15 each comprising a reinforcing wall ridge 51 projecting downward from an upper wall 11 integrally therewith and brazed to a lower wall 12, and reinforcing walls 15 each comprising a reinforcing wall ridge 52 projecting upward from the lower wall 12 integrally therewith and brazed to the upper wall 11, the former walls 15 and the latter walls 15 being arranged alternately in the left-right direction. With the exception of this feature, the heat exchange tube 50 is the same as the heat exchange tube 4 shown in FIG. 2. The portions where the ridges 51 are brazed to the lower wall 12, and those where the ridges 51 are brazed to the upper wall 11 are inside joints.

The flat heat exchange tube 50 is fabricated from a metal plate 55 shown in FIG. 22(a). The metal plate 55 comprises an aluminum brazing sheet having a brazing material layer over opposite surfaces thereof. The metal plate has reinforcing wall ridges 51, 52 projecting upward from an upper wall forming portion 26 and a lower wall forming portion 27 integrally therewith and arranged in the left-right direction at a predetermined spacing, and the reinforcing wall ridges 51 on the upper wall forming portion 26 and the reinforcing wall ridges 52 on the lower wall forming portion 27 are positioned asymmetrically about the center line of the metal plate with respect to the widthwise direction. The ridges 51, 52 have the same height, which is about twice the height of side wall ridges 17, 18. With the exception of these features, the metal plate 55 is the same as the metal plate 25 shown in FIG. 3.

The flat heat exchange tube 50 is fabricated by progressively folding the metal plate 55 at the left and right opposite side edges of the connecting portion 28 by the roll forming process [see FIG. 22(b)], finally folding the plate 55 to the shape of a hairpin to butt the side wall ridges 17, 18 against each other, force the projection 31 into the groove 32, bring the reinforcing wall ridges 51 of the upper wall forming portion 26 into contact with the lower wall forming portion 27 and the reinforcing wall ridges 52 of the lower wall forming portion 27 into contact with the upper wall forming portion 26, and obtain a folded body 33 [see FIG. 22(c)], and brazing the side wall ridges 17, 18 to each other at their top ends, the reinforcing wall ridges 51 of the upper wall forming portion 26 to the lower wall forming portion 27 and the reinforcing wall ridges 52 of the lower wall forming portion 27 to the upper wall forming portion 26. At this time, the left side wall 13 is formed by the side wall ridges 17, 18 brazed to each other, the right side wall 14 by the connecting portion 28, the upper wall 11 by the upper wall forming portion 26, the lower wall 12 by the lower wall forming portion 27, and the reinforcing walls 15 by the respective reinforcing wall ridges 51, 52.

Figure 23:
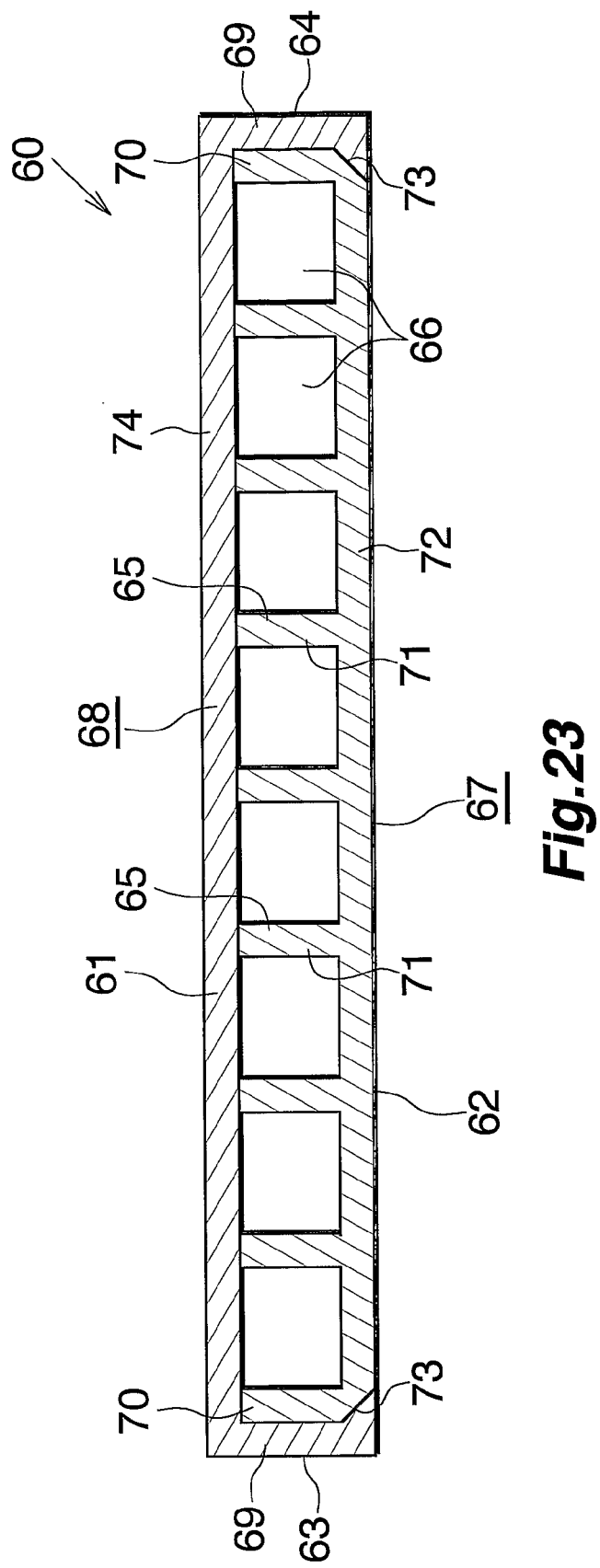
FIG. 23 is a cross sectional view showing another modified flat heat exchange tube for use in the heat exchanger of FIG. 1.
Figure 24:
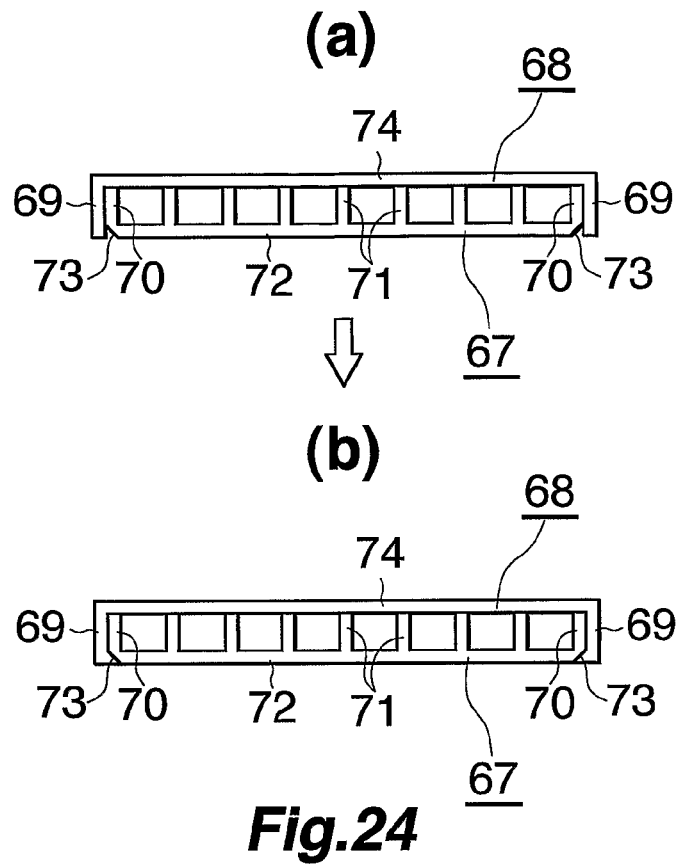
FIG. 24 is a diagram showing a process for fabricating the flat heat exchange tube of FIG. 23.

FIG. 23 shows a flat heat exchange tube 60, which comprises flat upper and lower walls 61, 62, left and right opposite side walls 63, 64 of double structure interconnecting the upper and lower walls 61, 62 at the respective left and right side edges thereof, and a plurality of reinforcing walls 65 interconnecting the upper and lower walls 61, 62, extending longitudinally of the tube and spaced from one another as positioned between the left and right side walls 63, 64. The tube 60 has parallel fluid passageways 66 formed inside thereof. The flat tube 60 is provided by a lower component member 67 of aluminum constituting the lower wall 62, left and right sidewalls 63, 64 and reinforcing walls 65, and an upper component member 68 of aluminum plate constituting the upper wall 61 and the left and right side walls 63, 64. Although not shown, each reinforcing wall 65 has a plurality of communication holes for holding adjacent fluid passageways 66 in communication with each other. When seen from above, all the communication holes are in a staggered arrangement.

Each of the opposite side walls 63, 64 is made from a downward side wall ridge 69 projecting downward from each of the left and right side edges of the upper wall 61 integrally therewith and an upward side wall ridge 70 projecting upward from each of the left and right side edges of the lower wall 62 integrally therewith, by brazing the ridges 69, 70 as lapped over each other, with the downward ridge 69 positioned on the outer side. The upward ridge 70 has its upper end brazed to the upper wall 61. The reinforcing walls 65 are formed from reinforcing wall ridges 71 projecting upward from the lower wall 62 integrally therewith, by brazing the ridges 71 to the upper wall 61. The portions where the ridges 71 are brazed to the upper wall 61 are inside joints.

With reference to FIG. 24(a), the lower component member 67 comprises a flat lower wall forming portion 72, upward side wall ridges 70 projecting upward respectively from opposite side edges of the lower wall forming portion 72 integrally therewith, and a plurality of reinforcing wall ridges 71 projecting upward from the lower wall forming portion 72 integrally therewith, extending longitudinally of the tube and spaced from one another as positioned between the side wall ridges 70. The lower component member 67 has a slope 73 formed at each of opposite side edges of its lower surface and slanting laterally outwardly upward.

As shown in FIG. 24(a), the upper component member 68 is made from an aluminum brazing sheet having a brazing material layer over opposite sides thereof by a suitable method such as roll forming, press work or rolling. The upper component member 68 comprises a flat upper wall forming portion 74, and downward side wall ridges 69 downwardly projecting respectively from opposite side edges of the upper wall forming portion 74 integrally therewith and to be lapped over the outer side of the respective side wall ridges 70 of the lower component member 67. The upper wall forming portion 74 of the upper component member 68 has a slightly larger width than the lower component member 67 so that the upper component member 68 is fitted over the member 67.

The upper component member 68 is placed over the lower component member 67 with the downward side wall ridges 69 lapped over the respective upward side wall ridges 70 externally thereof and with the upper ends of the reinforcing wall ridges 71 in contact with the upper wall forming portion 74 of the member 68 [see FIG. 24(a)]. The lower ends of the downward side wall ridges 69 are then deformed and brought into intimate contact with the respective slopes 73, whereby the two component members 67, 68 are temporarily held together [see FIG. 24(b)]. Each adjacent pairs of side wall ridges 69, 70 are thereafter brazed to each other, the upper ends of the upward side wall ridges 70 and the reinforcing wall ridges 71 to the upper wall forming portion 74, and the deformed portions of the downward side wall ridges 69 to the respective slopes 73. In this way, the flat tube 60 is fabricated. At this time, the left and right side walls 63, 64 are formed by the respective brazed pairs of ridges 69, 70, the upper wall 61 by the upper wall forming portion 74, the lower wall 62 by the lower wall forming portion 72, and the reinforcing walls 65 by the reinforcing wall ridges 71.

Like the heat exchange tube 4 shown in FIG. 2, the heat exchange tubes 50, 60 shown in FIGS. 21 and 23 are used for condensers for use in refrigeration cycles which comprise a compressor, condenser, evaporator and pressure reducing device and wherein a chlorofluorocarbon refrigerant is used. Further the heat exchange tubes 4, 50, 60 shown in FIGS. 2, 21 and 23 may be used for evaporators for use in refrigeration cycles which comprise a compressor, condenser, evaporator and pressure reducing device and wherein a chlorofluorocarbon refrigerant is used.

Furthermore, the heat exchange tubes 4, 50, 60 shown in FIGS. 2, 21 and 23 may be used for gas coolers or evaporators for use in refrigeration cycles which comprise a compressor, gas cooler, evaporator, pressure reducing device and intermediate heat exchanger for subjecting to heat exchange the refrigerant flowing out of the gas cooler and the refrigerant flowing out of the evaporator and wherein $CO_2$ or like supercritical refrigerant is used. The refrigeration cycle is installed in vehicles, for example, in motor vehicles.

Figure 25:
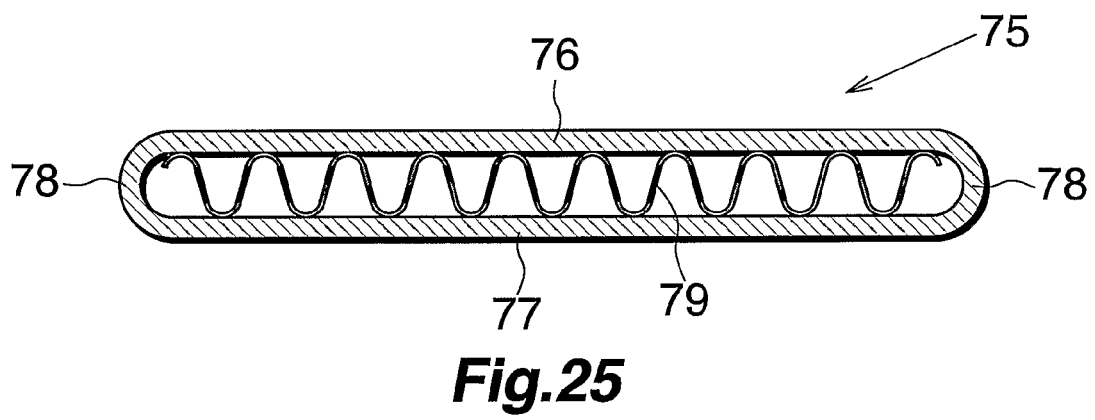
FIG. 25 is a cross sectional view showing another modified flat heat exchange tube for use in the heat exchanger of FIG. 1.

FIG. 25 shows a flat heat exchange tube 75, which comprises flat upper and lower walls 76, 77, and left and right side walls 78 interconnecting the upper and lower walls 76, 77 at the left and right side edges thereof and formed integrally with the walls 76, 77. The tube has disposed inside thereof an inner corrugated fin 79 having crest portions and furrow portions which extend longitudinally of the tube 75. The flat heat exchange tube 75 is in the form of an electro-resistance welded tube made of an aluminum brazing sheet having a brazing material layer over opposite surfaces thereof. The inner fin 79 is made from an aluminum material and has their crest portions and furrow portions brazed to the upper and lower walls 76, 77. The portions where the inner fin 79 is brazed to the upper and lower walls 76, 77 are inside joints.

Figure 26:
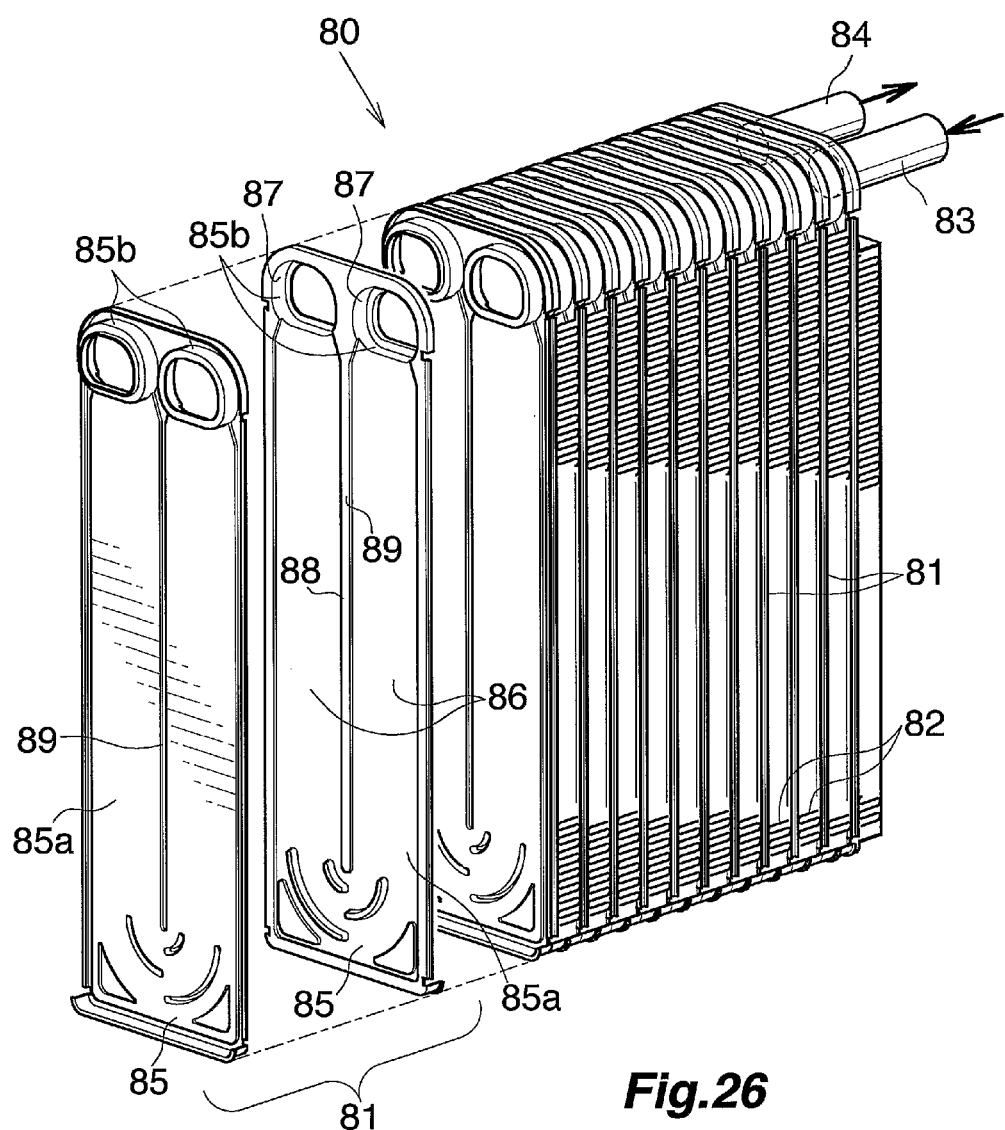
FIG. 26 is an exploded perspective view showing a modified heat exchanger to be inspected for pressure resistance by the method and apparatus of the invention, inner fins being not shown.
Figure 27:
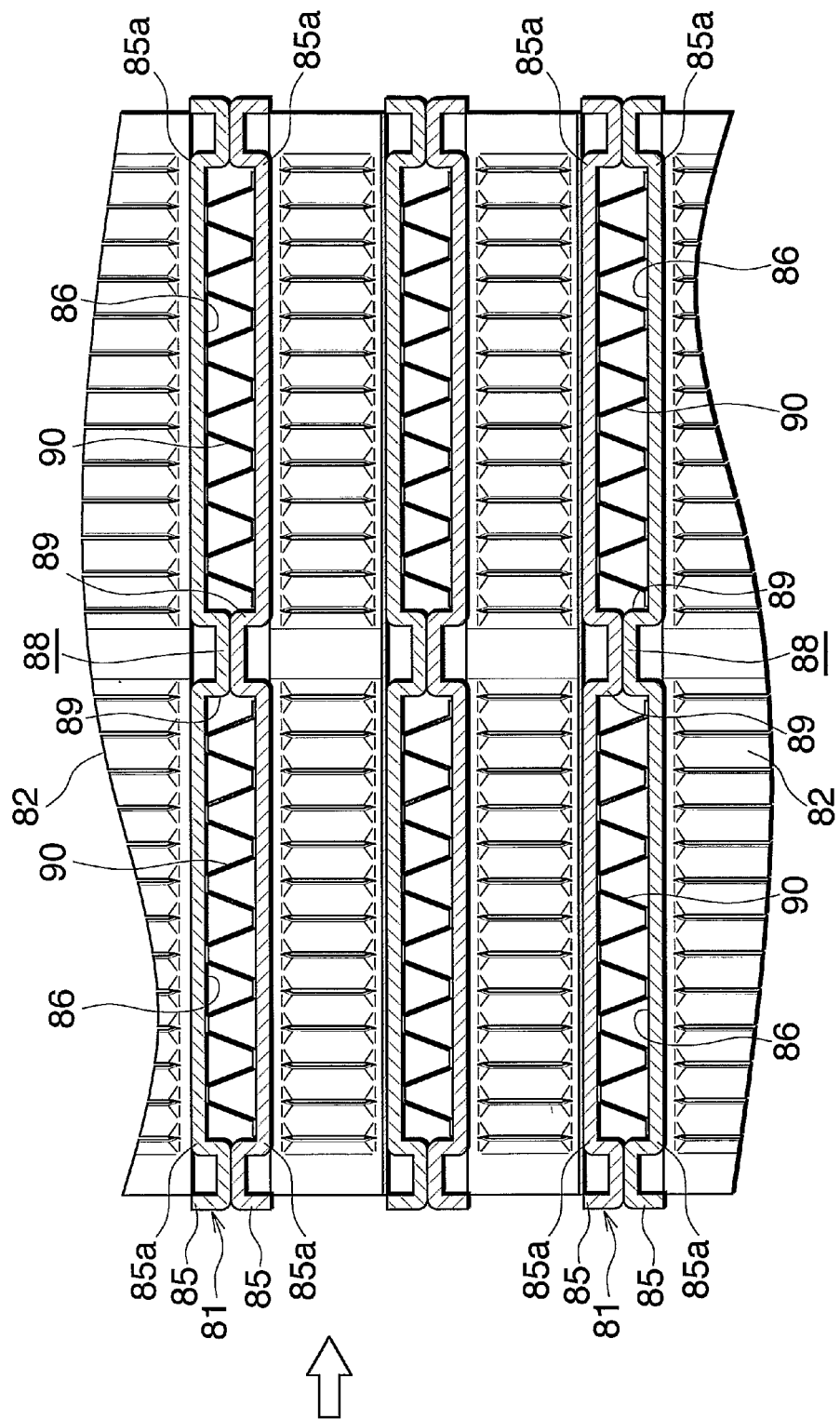
FIG. 27 is an enlarged cross sectional view showing flat hollow bodies of the heat exchanger of FIG. 26.

FIGS. 26 and 27 show another example of heat exchanger to be inspected for pressure resistance by the method of the invention.

With reference to FIGS. 26 and 27, a heat exchanger 80 for use as an evaporator in motor vehicle air conditioners comprises a plurality of flat hollow bodies 81 (hollow refrigerant channel portions) arranged in parallel and brazed to and communicating with one another at their upper ends, and corrugated fins 82 made of an aluminum material, arranged in air passing clearances between respective adjacent pairs of flat hollow bodies 81 and each brazed to the hollow bodies adjacent thereto. A refrigerant flowing into the heat exchanger through a fluid inlet 83 flows through all the flat hollow bodies 81 and flows out via a fluid outlet 84.

Each flat hollow body 81 is made from two plates 85 made of a brazing aluminum sheet having a brazing material layer over opposite surfaces thereof, by brazing the two plates 85 to each other at their peripheral edge portions. The two plates 85 define therebetween two bulging refrigerant channels 86 divided by a partition wall 88, and two header forming portions 87 bulging to a greater height than the channels 86 and communicating with the upper end of each of the channels 86.

The partition wall 88 extends between the two bulging header forming portions 87 to a lower end portion of the body 81, and the two bulging channels 86 are in communication at the lower end portion. The partition wall 88 is formed from partition ridges 89 formed on the respective plates 85 between the refrigerant channels 86 by brazing the ridges 89 to each other. The brazed portions of the ridges 89 of the two plates 85 provide an inside joint. Disposed in each of the refrigerant channels 86 of the flat hollow body 81 is a corrugated inner fin 90 made of a bare aluminum material and having crest portions and furrow portions which extend longitudinally of the fin. The inner fin 90 is brazed to the two plates 85 utilizing the brazing material layer of the plates 85, and the portions of the fin 90 brazed to the two plates 85 are also inside joints. A plurality of hollow bodies 81 are stacked in layers and brazed to one another, with the opposed outer surfaces of each adjacent pair of bulging header forming portions in contact with each other. The portions of each adjacent pair of flat hollow bodies 81 which portions correspond to the channels 86 define an air passing clearance therebetween. The corrugated fin 82 is disposed in this air passing clearance and brazed to the hollow bodies 81.

The heat exchanger 80 serves as an evaporator and provides a refrigeration cycle along with a compressor and a condenser, and the cycle is installed, for example, in motor vehicles as an air conditioner.

Figure 28:
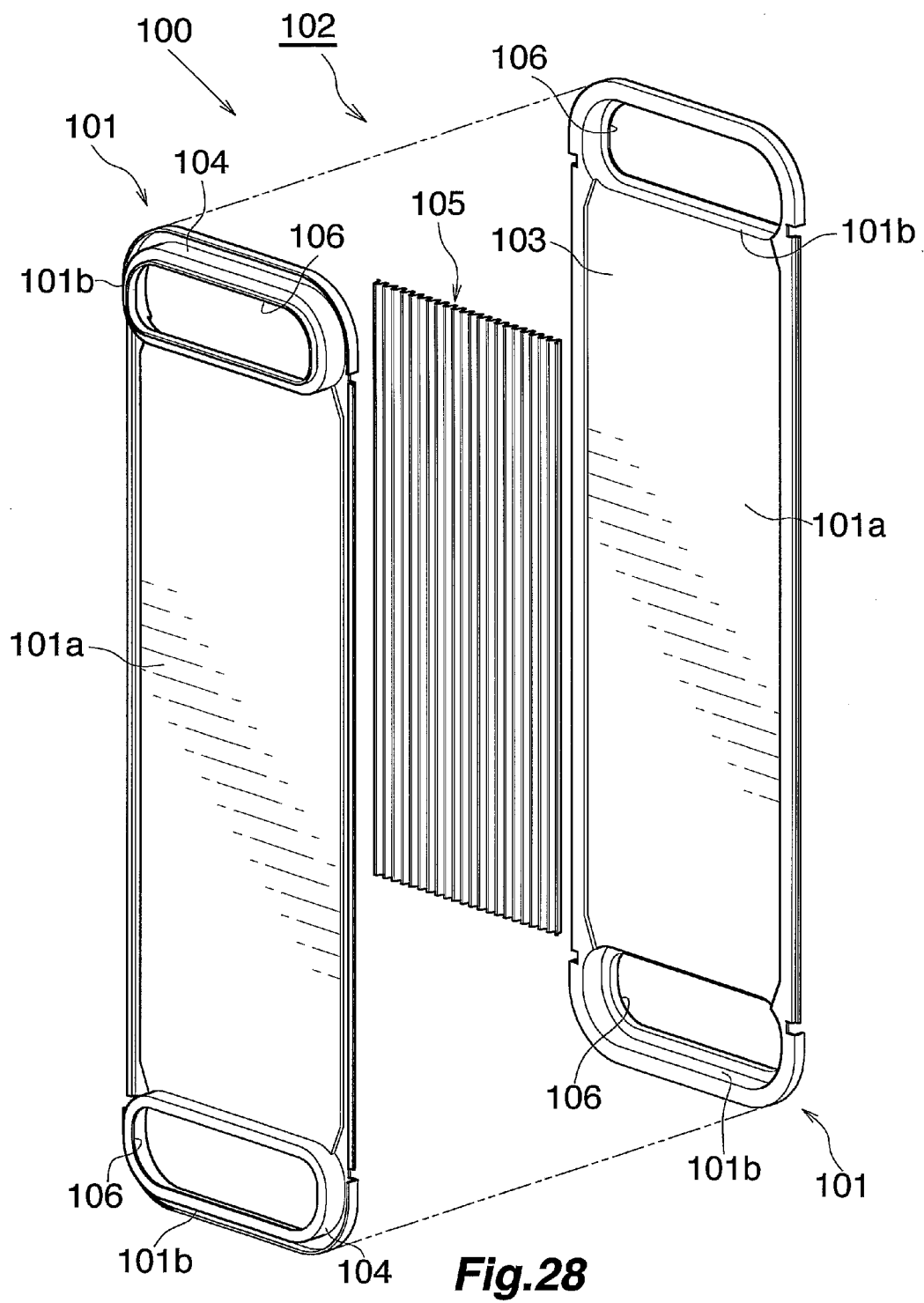
FIG. 28 is an exploded perspective view showing another example of heat exchange tube of a heat exchanger to be used as a motor vehicle air conditioner and to be inspected for pressure resistance by the method of the invention.
Figure 29:
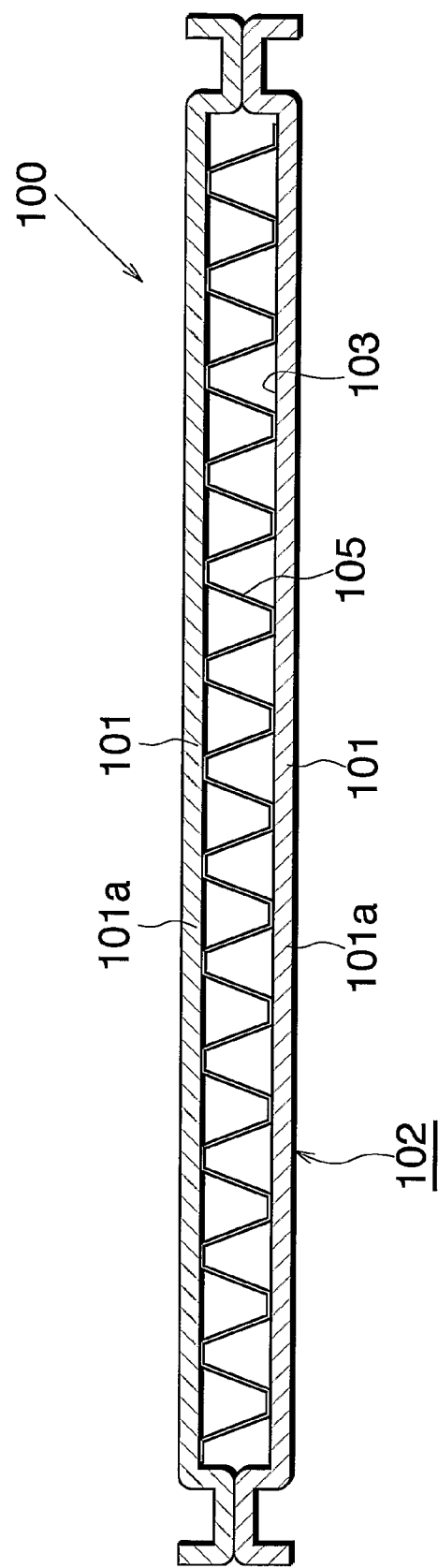
FIG. 29 is an enlarged cross sectional view of the heat exchange tube of FIG. 28.

FIGS. 28 and 29 show another example of heat exchange tube serving an a refrigerant channel portion for use in a heat exchanger which is to be inspected by the method of the invention for pressure resistance and to be used as a motor vehicle air conditioner.

With reference to FIGS. 28 and 29, a heat exchange tube 100 comprises a flat hollow body 102 which is made from two plates 101 made of a brazing aluminum sheet having a brazing material layer over opposite surface thereof, by brazing the two plates to each other at their peripheral edge portions. Between the two plates 101, the hollow body has a bulging refrigerant channel 103 extending vertically, and a header forming portion 104 bulging to a larger height than the channel 103 and communicating with each of upper and lower ends of the channel 103.

Provided within the refrigerant channel 103 of the hollow body 102 is a corrugated inner fin 105 made of an aluminum material and having crest portions and furrow portions extending vertically. The inner fin 105 is brazed to the two plates 101 utilizing the brazing material layer of the plates 101, and the portions of the fin 105 brazed to the plates 101 are inside joints. The top walls defining the respective two header forming portions 104 of the flat hollow body 102 are each formed with a through hole 106. As is the case with the heat exchanger 80 shown in FIGS. 26 and 27, a plurality of flat hollow bodies 102 are stacked in layers, with the opposed outer surfaces of each adjacent pair of walls of the bulging header forming portions 104 in contact with each other, so that the corresponding header forming portions 104 of each adjacent pair of hollow bodies 102 communicate with each other through the holes 106. The portions of each adjacent pair of flat hollow bodies 102 which portions correspond to the channels 103 define an air passing clearance therebetween. The corrugated fin (not shown) is disposed in this clearance and brazed to the hollow bodies 102. In this case, no through hole 106 is formed in the top walls of header forming portions 104 of a flat hollow body provided at a suitable position, and a refrigerant flowing in through a fluid inlet provided at the suitable position flows through all flat hollow bodies 102 and flows out of the heat exchanger.

The heat exchanger 1 can be inspected for pressure resistance also by the following method.

The interior of the heat exchanger 1 is pressurized first, and the exchanger 1 is then irradiated with light from one side thereof and visually inspected from the other side thereof.

The corrugated fins 6 and/or the heat exchange tubes 4 of the heat exchanger 1 are visually inspected for deformation by this method.

INDUSTRIAL APPLICABILITY

The present invention provides pressure resistance inspecting method and apparatus which are suitable for inspecting heat exchangers having a plurality of hollow refrigerant channel portions arranged in parallel and each having joints inside thereof, air passing clearances between respective adjacent pairs of refrigerant channel portions, and fins arranged in the respective air passing clearances.

The invention claimed is:

1. A method of inspecting a heat exchanger for pressure resistance, the heat exchanger having a plurality of hollow refrigerant channel portions arranged in parallel and each having joints inside thereof, air passing clearances between respective adjacent pairs of refrigerant channel portions, and fins arranged in the respective air passing clearances,
the method of inspecting a heat exchanger for pressure resistance comprising:
pressurizing interior of the heat exchanger,
irradiating the heat exchanger with light from one side thereof with respect to the direction of passage of air therethrough and capturing an image of the heat exchanger by image pickup means from the other side thereof before and after the pressurization,
dividing each of the images into a plurality of dots, and
judging the pressure resistance of the heat exchanger based on luminance data as to the dots of the images obtained before and after the pressurization respectively.

2. A method of inspecting a heat exchanger for pressure resistance according to claim 1 which includes capturing a plurality of images of a portion of the heat exchanger by the image pickup means from a plurality of directions, dividing each of the images into dots, and using luminance data as to the dots of the plurality of images of the same portion as a reference for judgment.

3. A method of inspecting a heat exchanger for pressure resistance according to claim 1 which includes capturing a monochromatic image of the heat exchanger by the image pickup means before and after the pressurization, dividing each of the monochromatic images into a plurality of dots, converting luminance data as to the dots of each of the images obtained before and after the pressurization into binary data items of white areas and black areas with reference to a predetermined reference value, counting the number of black areas of each monochromatic image, and using an increase in the number of black areas after the pressurization from the number of black areas before the pressurization as a reference for judgment.

4. A method of inspecting a heat exchanger for pressure resistance according to claim 1 which includes capturing a plurality of monochromatic images of a portion of the heat exchanger by the image pickup means from a plurality of directions, dividing each of the images into dots, converting luminance data as to the dots of each of the images obtained before and after the pressurization into binary data items of white areas and black areas with reference to a predetermined reference value, counting the number of black areas of each monochromatic image, and using an increase in the total number of black areas of all monochromatic images after the pressurization from the total number of black areas of all monochromatic images before the pressurization as a reference for judgment.

5. A method of inspecting a heat exchanger for pressure resistance according to claim 1 which includes capturing a monochromatic image of the heat exchanger by the image pickup means before and after the pressurization, dividing each the monochromatic images into a plurality of dots, converting luminance data as to the dots of each of the images obtained before and after the pressurization into binary data items of white areas and black areas with reference to a predetermined reference value to extract a pattern of white areas and black areas in each monochromatic image, and using the patterns obtained before and after the pressurization as a reference for judgment.

6. A method of inspecting a heat exchanger for pressure resistance, the heat exchanger having a plurality of hollow refrigerant channel portions arranged in parallel and each having joints inside thereof, air passing clearances between respective adjacent pairs of refrigerant channel portions, and fins arranged in the respective air passing clearances,
the method of inspecting a heat exchanger for pressure resistance comprising:
irradiating the heat exchanger with light from one side thereof with respect to the direction of passage of air therethrough,
capturing an image of the heat exchanger by image pickup means from the other side thereof,
dividing the image into a plurality of dots,
thereafter pressurizing interior of the heat exchanger,
capturing an image of the heat exchanger by image pickup means from the other side thereof continuously or intermittently after the start of the pressurization,
dividing the image into a plurality of dots, and
judging the pressure resistance of the heat exchanger based on luminance data as to the dots of the image obtained before the pressurization and on continuous variations or intermittent variations in luminance data as to the dots of the image obtained after the pressurization.

7. A method of inspecting a heat exchanger for pressure resistance according to claim 6 wherein the pressure to be applied to the interior of the heat exchanger is controlled based on continuous variations or intermittent variations in the luminance data as to the dots of the image obtained after the pressurization.

8. An apparatus for inspecting a heat exchanger for pressure resistance, the heat exchanger having a plurality of hollow refrigerant channel portions arranged in parallel and each having joints inside thereof, air passing clearances between respective adjacent pairs of refrigerant channel portions, and fins arranged in the respective air passing clearances,
the inspecting apparatus comprising:
pressurizing means for pressurizing interior of the heat exchanger,
irradiating means disposed on one side of the heat exchanger with respect to the direction of passage of air therethrough for irradiating the heat exchanger with light,
image pickup means for capturing an image of the heat exchanger from the other side of the heat exchanger opposite to the irradiating means with respect to the direction of passage of air, and
processing means for dividing the images obtained by the image pickup means into a plurality of dots before and after the pressurization by the pressurizing means and judging the pressure resistance of the heat exchanger based on luminance data as to the dots of each of the images.

9. A heat exchanger fabrication line comprising an apparatus according to claim 8.

10. An apparatus for inspecting a heat exchanger for pressure resistance according to claim 8 wherein the image pickup means captures a plurality of images of a portion of the heat exchanger from a plurality of directions, and the processing means divides each of the images of the same portion into a plurality of dots and judges the pressure resistance of the heat exchanger based on luminance data as to the dots of each image.

11. An apparatus for inspecting a heat exchanger for pressure resistance according to claim 8 wherein the processing means divides a monochromatic image of the heat exchanger captured by the image pickup means before and after the pressurization into plurality of dots, converts luminance data as to the dots of each of the monochromatic images obtained before and after the pressurization into binary data items of white areas and black areas with reference to a predetermined reference value, counts the number of black areas of each monochromatic image, and judges the pressure resistance of the heat exchanger based on an increase in the number of black areas after the pressurization from the number of black areas before the pressurization.

12. An apparatus for inspecting a heat exchanger for pressure resistance according to claim 8 wherein the image pickup means captures a plurality of monochromatic images of a portion of the heat exchanger from a plurality of directions, and the processing means divides each of the monochromatic images of the same portion into dots, converts luminance data as to the dots of each image into binary data items of white areas and black areas with reference to a predetermined reference value, counts the number of black areas of each monochromatic image, and judges the pressure resistance of the heat exchanger based on an increase in the total number of black areas of all monochromatic images after the pressurization from the total number of black areas of all monochromatic images before the pressurization.

13. An apparatus for inspecting a heat exchanger for pressure resistance according to claim 8 wherein the processing means divides each of the monochromatic images of the heat exchanger captured by the image pickup means before and after the pressurization into dots, converts luminance data as to the dots of each of the images into binary data items of white areas and black areas with reference to a predetermined reference value to extract a pattern of white areas and black areas in each monochromatic image, and judges the pressure resistance of the heat exchanger based on the patterns obtained before and after the pressurization.

14. An apparatus for inspecting a heat exchanger for pressure resistance according to claim 8 wherein reflecting means is disposed on the other side of the heat exchanger opposite to the irradiating means with respect to the direction of passage of air for reflecting the light from the irradiating means at least once, and the image pickup means captures images reflected at the reflecting means.

15. An apparatus for inspecting a heat exchanger for pressure resistance according to claim 8 wherein the processing means judges the pressure resistance of the heat exchanger based on the luminance data as to the dots of the image before the pressurization and on continuous variations or intermittent variations in the luminance data as to the dots of the image after the pressurization.

16. An apparatus for inspecting a heat exchanger for pressure resistance according to claim 15 wherein the processing means divides each of monochromatic images of the heat exchanger captured by the image pickup means before and after the pressurization into a plurality of dots, converts luminance data as to the dots of each of the images into binary data items of white areas and black areas with reference to a predetermined reference value, counts the number of black areas in each monochromatic image and judges the pressure resistance of the heat exchanger based on the number of black areas before the pressurization and on continuous variations or intermittent variations in the number of black areas after the pressurization.

17. An apparatus for inspecting a heat exchanger for pressure resistance according to claim 15 wherein the image pickup means captures a plurality of monochromatic images of a portion of the heat exchanger from a plurality of directions, and the processing means divides each of the images of the same portion into a plurality of dots, converts luminance data as to the dots of each image into binary data items of white areas and black areas with reference to a predetermined reference value, counts the number of black areas in each monochromatic image and judges the pressure resistance of the heat exchanger based on the number of black areas before the pressurization and on continuous variations or intermittent variations in the number of black areas after the pressurization.

18. An apparatus for inspecting a heat exchanger for pressure resistance according to claim 15 wherein the processing means divides each of monochromatic images of the heat exchanger captured by the image pickup means before and after the pressurization into a plurality of dots, converts luminance data as to the dots of each of the images into binary data items of white areas and black areas with reference to a predetermined reference value to extract a pattern of white areas and black areas in each monochromatic image, and judges the pressure resistance of the heat exchanger based on the pattern before the pressurization and on continuous variations or intermittent variations in the pattern after the pressurization.

19. An apparatus for inspecting a heat exchanger for pressure resistance according to claim 15 wherein the processing means controls the pressure to be applied to the interior of the heat exchanger by the pressurizing means based on continuous variations or intermittent variations in the luminance data as to the dots of the image obtained after the pressurization.

* * * * *